United States Patent [19]
Houghton et al.

[11] Patent Number: 5,932,219
[45] Date of Patent: Aug. 3, 1999

[54] HEPATITIS DELTA VIRUS P27$^\delta$ AND P24$^\delta$ VACCINE

[75] Inventors: Michael Houghton, Danville; Kang-Sheng Wang, Oakland; Qui-Lim Choo, El Cerrito; Amy Joan Weiner, Berkeley; Lacy Rasco Overby, Alamo, all of Calif.

[73] Assignee: Chiron Corporation, Emeryville, Calif.

[21] Appl. No.: 08/450,689

[22] Filed: May 25, 1995

Related U.S. Application Data

[62] Division of application No. 08/262,667, Jun. 20, 1994, abandoned, which is a continuation of application No. 08/097,519, Jul. 27, 1993, Pat. No. 5,389,528, which is a continuation of application No. 07/932,920, Aug. 20, 1992, abandoned, which is a continuation of application No. 07/765,917, Sep. 25, 1991, abandoned, which is a division of application No. 07/053,991, May 22, 1987, abandoned, which is a continuation-in-part of application No. 06/875, 337, Jun. 17, 1986, abandoned.

[51] Int. Cl.$^6$ ........................... A61K 39/29; A61K 39/12; C12N 15/51; C07K 1/00
[52] U.S. Cl. .................................. 424/189.1; 424/228.1; 424/204.1; 530/350; 530/826; 435/69.3
[58] Field of Search ................................. 435/69.1, 69.3, 435/69.7, 71.2, 172.3, 235.1, 236, 252.3, 320.1, 267; 424/159.1, 186.1, 192.1, 204.1, 225.1, 228.1, 227.1; 530/350, 388.21, 388.3, 826; 436/86; 536/23.72, 23.1

[56] References Cited

U.S. PATENT DOCUMENTS

| | | |
|---|---|---|
| 4,619,896 | 10/1986 | Shattuck et al. . |
| 4,710,463 | 12/1987 | Murray . |
| 4,959,462 | 9/1990 | Dijkema et al. . |
| 5,225,347 | 7/1993 | Goldberg et al. . |
| 5,378,814 | 1/1995 | Houghton et al. . |

FOREIGN PATENT DOCUMENTS

| | | |
|---|---|---|
| 175261 | 3/1986 | European Pat. Off. . |
| 182442 | 5/1986 | European Pat. Off. . |
| 234050 | 9/1987 | European Pat. Off. . |
| 251575 | 1/1988 | European Pat. Off. . |
| 3116882 A1 | 1/1982 | Germany . |
| 8402392 | 7/1984 | Netherlands . |

OTHER PUBLICATIONS

Bergmann et al., "Antigens of hepatitis delta virus in the liver and serum of humans and animals," *J. Infect. Diseases* 154(4):702–706 (1986).
Bonino et al., "Hepatitis delta virus: protein composition of delta antigen and its hepatitis B virus–derived envelope," *Hepatology* 1:127–131 (1981).
Bonino et al., "Hepatitis delta virus: protein composition of delta antigen and its hepatitis B virus–derived envelope," *J. Virol.* 58(3):945–950 (1986).
Chen et al., "Structure and replication of the genome of the hepatitis delta virus," *Proc. Natl. Acad. Sci. USA* 83: 8774–8778 (1986).
Denniston et al., "Cloned fragment of the hepatitis delta virus RNA genome: Sequence and diagnostic application," *Science* 232:873–875 (1986).
Denniston et al., *Biochem. Genetics* 105:ref. 1518y (1986).
Hallewell et al. *Proc. Natl. Acad. Sci* 13(6):2017–2034.
Hoyer et al., "Properties of Delta–Associated Ribonucleic Acid," presented at the Turin Symposium, 1983.
Hoyer et al., "Evidence for non–A, non–B viruses," *Chem. Abstracts*: ref. 171213j (1984).
Jacobson et al., "Epidemiology and clinical impact of hepatitis D virus (Delta) infection," *Hepatology* 5:188–191 (1985).
Kos et al., "The hepatitis delta virus possesses a circular RNA," *Nature* 323(6088):558–560 (1986).
Rizzetto et al., "Immunofluorescence detection of new antigen–antibody system (delta/anti–delta) associated to hepatitis B virus in liver and in serum of HBsAg carriers," *Gut* 18:997–1003 (1977).
Rizzetto et al., "The hepatitis B virus–associated delta antigen: isolation from liver development of solid–phase radioimmunoassays for delta antigen and anti–delta and partial characterization of delta antigen," *Proc. Natl. Acac. Sci. USA* 77:6124–6128 (1980).
Rizzetto et al., "The hepatitis B virus–associated delta antigen: isolation from liver development of solid–phase radioimmunoassays for delta antigen and anti–delta and partial characterization of delta antigen," *J. Immunol.* 125(1):318–324 (1980).
Rizzetto et al., "Delta hepatitis—present status," (1985) *J. Hepatology* 1:187–193.
Schiff et al., "Delta agent: Another hepatitis virus," *Diagnostic Medicine*, pp. 17–22 (1985).
Valenzuela et al., "Synthesis and assembly of hepatitis B virus surface antigen particles in yeast," *Nature* 298:347–350 (1982).
Wang et al., "Structure, sequence and expression of the hepatitis delta viral genome," *Nature* 323(6088):508–514 (1986).
Wickens et al., *J. Biol. Chem.* 253:2483–2375 (1978).
Gerin et al., Viral Hepatitis & Liver Disease, International Symposium on Viral Hepatitis & Liver Disease (8th:1993: Tokyo, Japan) Springer–Verlag Tokyo 1994, pp. 38–41.
Karayiannis et al., Hepatitis Delta Virus, vol., Wiley–Liss Inc, vol. 382, pp. 193–199, 1993.
Ponzetto et al. Hepatitis Delta Virus (1993) Wiley–Liss, Inc., 270–210.

*Primary Examiner*—Marian C. Knode
*Assistant Examiner*—Jay Williams
*Attorney, Agent, or Firm*—Roberta L. Robins; Barbara G. McClung; Robert P. Blackburn

[57] ABSTRACT

The entire genome of the hepatitis D virus has been shown to be a circular single-stranded RNA of 1679 bases. Several open reading frames in both the genomic and complementary strands indicate possible protein products. The products encoded in one open reading frame, ORF5, are identified as viral polypeptides p24$^\delta$ and p27$^\delta$, of which the nuclear δ antigens in HDV infected liver is comprised. These products, as well as others encoded in ORFs 1, 2, 6, and 7 are produced in recombinant expression systems. The ORF5 products, in particular, are useful for HDV diagnosis and vaccines.

4 Claims, 11 Drawing Sheets

```
                                                                    C
  1 CTTGAGCCAAGTTCCGAGCGAGGAGACGCGGGGGGAGGATCAGCTCCCGAGAGGGGATGT
    GAACTCGGTTCAAGGCTCGCTCCTCTGCGCCCCCTCCTAGTCGAGGGCTCTCCCCTACA

CACGGTAAAGAGCATTGGAACGTCGGAGAAACTACTCCCAAGAAGCAAAGAGAGGTCTCA
    GTGCCATTTCTCGTAACCTTGCAGCCTCTTTGATGAGGGTTCTTCGTTTCTCTCCAGAGT
121 GGAAGCGGACGAGATCCCCACAACGCCGGAGAATCTCTGGAAGGGGAAAGAGGAAGGTGG
    CCTTCGCCTGCTCTAGGGGTGTTGCGGCCTCTTAGAGACCTTCCCCTTTCTCCTTCCACC

AAGAAAAAGGGGCGGGCCTCCCGATCCGAGGGGCCCAACCTCCAGATCTGGAGAGCACTC
    TTCTTTTTCCCCGCCCGGAGGGCTAGGCTCCCCGGGTTGGAGGTCTAGACCTCTCGTGAG
                       T
241 CGGCCCGAAGGGTTGAGTAGCACCCAGAGGGAGGAATCCACTCGGAGATGAGCAGAGAAA
    GCCGGGCTTCCCAACTCATCGTGGGTCTCCCTCCTTAGGTGAGCCTCTACTCGTCTCTTT

TCACCTCCAGAGGACCCCTTCAGCGAACAAGAGGCGCTTCGAGCGGTAGGAGTAAGACCA
    AGTGGAGGTCTCCTGGGGAAGTCGCTTGTTCTCCGCGAAGCTCGCCATCCTCATTCTGGT
                                G                              C
361 TAGCGATAGGAGGAGATGCTAGGAGTAGGAGGAGACCGAAGCGAGGAGGAAAGTAAAGAA
    ATCGCTATCCTCCTCTACGATCCTCATCCTCCTCTGGCTTCGCTCCTCCTTTCATTTCTT

AGCAACGGGGCTAGCCGGTGGGTGTTCCGCCCCCGAGAGGGGACGAGTGAGGCTTATCC
    TCGTTGCCCCGATCGGCCACCCACAAGGCGGGGGGCTCTCCCCTGCTCACTCCGAATAGG
         T
481 CGGGGAACTCGACTTATCGTCCCCATCTAGCGGGACCCCGGACCCCCTTCGAAAGTGACC
    GCCCCTTGAGCTGAATAGCAGGGGTAGATCGCCCTGGGGCCTGGGGGAAGCTTTCACTGG
             A                                      T
    GGAGGGGGTGCTGGGAACACCGGGGACCAGTGGAGCCATGGGATGCCCCTCCCGATGCTC
    CCTCCCCCACGACCCTTGTGGCCCCTGGTCACCTCGGTACCCTACGGGGAGGGCTACGAG
       C                                                 A
601 GATTCCGACTCCCCCCCCCAAGGGTCGCCCAGGAATGGCGGGACCCCACTCTGCAGGGTC
    CTAAGGCTGAGGGGGGGGGTTCCCAGCGGGTCCTTACCGCCCTGGGGTGAGACGTCCCAG

CGCGTTCCATCCTTTCTTACCTGATGGCCGGCATGGTCCCAGCCTCCTCGCTGGCGCCGG
    GCGCAAGGTAGGAAAGAATGGACTACCGGCCGTACCAGGGTCGGAGGAGCGACCGCGGCC
721 CTGGGCAACATTCCGAGGGGACCGTCCCCTCGGTAATGGCGAATGGGACCCACAAATCTC
    GACCCGTTGTAAGGCTCCCCTGGCAGGGGAGCCATTACCGCTTACCCTGGGTGTTTAGAG

TCTAGATTCCGATAGAGAATCGAGAGAAAAGTGGCTCTCCCTTAGCCATCCGAGTGGACG
    AGATCTAAGGCTATCTCTTAGCTCTCTTTTCACCGAGAGGGAATCGGTAGGCTCACCTGC
841 TGCGTCCTCCTTCGGATGCCCAGGTCGGACCGCGAGGAGGTGGAGATGCCATGCCGACCC
    ACGCAGGAGGAAGCCTACGGGTCCAGCCTGGCGCTCCTCCACCTCTACGGTACGGCTGGG

GAAGAGGAAAGAAGGACGCGAGACGCAAACCTGTGAGTGGAAACCCGCTTTATTCACTGG
    CTTCTCCTTTCTTCCTGCGCTCTGCGTTTGGACACTCACCTTTGGGCGAAATAAGTGACC
                                                      OP GlnPro
```

FIG. 2A

```
                           T                                  T
 961 GGTCGACAACTCTGGGGAGAAAAGGGCGGATCGGCTGGGAAGAGTATATCCCATGGAAAT
     CCAGCTGTTGAGACCCCTCTTTTCCCGCCTAGCCGACCCTTCTCATATAGGGTACCTTTA
     ArgCysSerGlnProSerPheProProAspAlaProPheLeuIleAspTrpProPheG
                                                            AM

T
     CCCCGGTTTCCCCTGATGTCCAGCCCCTCCCCGGTCCGAGAGAAGGGGGACTCCGGGACT
     GGGGCCAAAGGGGACTACAGGTCGGGGAGGGGCCAGGCTCTCTTCCCCCTGAGGCCCTGA
     lyArgAsnGlyArgIleAspLeuGlyGluGlyThrArgSerPheProSerGluProValGly
                                                                 Gln

A
1081 CCCTGCAGACTGGGGACGAAGCCGCCCCCGGGCGCTCCCCTCGATCCACCTTCGAGGGGG
     GGGACGTCTGACCCCTGCTTCGGCGGGGGCCCGCGAGGGGAGCTAGGTGGAAGCTCCCCC
     GlnLeuSerProValPheGlyGlyGlyProAlaGlyArgSerGlyGlyGluLeuPro
                                                               Leu

T
     ATCACACCCCCAACCGGCGGGCCGGCTACTCTTCTTTCCCTTCTCTCGTCTTCCTCGGTC
     TAGTGTGGGGGTTGGCCGCCCGGCCGATGAGAAGAAAGGGAAGAGAGCAGAAGGAGCCAG
     IeValGlyGlyValProProGlyAlaValArgArgGluArgArgGluAspGluGluThrLeu
     Asn

1201 AACCTCCTGAGTTCCTCTTCTTCCTCCTTGCTGAGGTTCTTGCCTCCCGCCGATAGCTGC
     TTGGAGGACTCAAGGAGAAGAAGGAGGAACGACTCCAAGAACGGAGGGCGGCTATCGACG
     ArgArgLeuGluGluGluGluGluLysSerLeuAsnLysGlyGlyAlaSerLeuGlnL
                                                                  C
     TTCTTCTTGTTCTCGAGGGCCTTCCTTCGTCGGTGATCCTGCCTCTCCTTGTCGGTGAAT
     AAGAAGAACAAGAGCTCCCGGAAGGAAGCAGCCACTAGGACGGAGAGGAACAGCCACTTA
     ysLysLysAsnGluLeuAlaLysArgArgArgHisAspGlnArgGluLysAspThrPheGly
                                                                 Arg

1321 CCTCCCCTGAGAGGCCTCTTCCTAGGTCCGGAGTCTACCTCCATCTGGTCCGTTCGGGCC
     GGAGGGGACTCTCCGGAGAAGGATCCAGGCCTCAGATGGAGGTAGACCAGGCAAGCCCGG
     GlyArgLeuProArgLysArgProGlySerAspValGluMetGlnAspThrArgAlaA

G
     CTCTTCGCCGGGGGAGCCCCCTCTCCATCCTTATCCTTCTTTCCGAGAATTCCTTTGATG
     GAGAAGCGGCCCCCTCGGGGGAGAGGTAGGAATAGGAAGAAAGGCTCTTAAGGAAACTAC
     rgLysAlaProProAlaGlyGluGlyAspLysAspLysLysGlyLeuIleGlyLysIleAsn

C
1441 TTCCCCAGCCAGGGATTTTCGTCCTCAATCTTTTTGAGTTTCTTCTTTGTCTTCCGGAGG
     AAGGGGTCGGTCCCTAAAAGCAGGAGTTAGAAAAACTCAAAGAAGAAACAGAAGGCCTCC
     GlyLeuTrpProAsnGluAspGluIleLysLysLeuLysLysLysThrLysArgLeuA

TCTCTCTCGAGTTCCTCTAACTTCTTTCTTCCGGCCACCCACTGCTCGAGGATCTCTTCT
     AGAGAGAGCTCAAGGAGATTGAAGAAAGAAGGCCGGTGGGTGACGAGCTCCTAGAGAAGA
     spArgGluLeuGluGluLeuLysLysArgGlyAlaValTrpGlnGluLeuIleGluGluArg

C
1561 CTCCCTCCGCGGTTCTTCCTCGACTCGGACCGGCTCATCTCGGCTAGAGGCGGCAGTCCT
     GAGGGAGGCGCCAAGAAGGAGCTGAGCCTGGCCGAGTAGAGCCGATCTCCGCCGTCAGGA
     GlyGlyArgAsnLysArgSerGluSerArgSerMetGluAlaLeuProProLeuGly

G
     CAGTACTCTTACTCTTTTCTGTAAAGAGGAGACTGCTGGACTCGCCGCCCGAGCCCAAG [CTT]
     GTCATGAGAATGAGAAAAGACATTTCTCCTCTGACGACCTGAGCGGCGGGCTCGGGTTC [GAA]
     < Orf 5
```

FIG. 2B

```
        GlyLeuProProLeuAlaGluMetSerArgSerGluSerArgLysAsnArgGlyGlyArg
  1     GGACTGCCGCCTCTAGCCGAGATGAGCCGGTCCGAGTCGAGGAAGAACCGCGGAGGGAGA
                   ---                                      G

GluGluIleLeuGluGlnTrpValAlaGlyArgLysLysLeuGluGluLeuGluArgAsp
 61     GAAGAGATCCTCGAGCAGTGGGTGGCCGGAAGAAAGAAGTTAGAGGAACTCGAGAGAGAC

LeuArgLysThrLysLysLysLeuLysLysIleGluAspGluAsnProTrpLeuGlyAsn
121     CTCCGGAAGACAAAGAAGAAACTCAAAAAGATTGAGGACGAAAATCCCTGGCTGGGGAAC
                                                                   G

IleLysGlyIleLeuGlyLysLysAspLysAspGlyGluGlyAlaProProAlaLysArg
181     ATCAAAGGAATTCTCGGAAAGAAGGATAAGGATGGAGAGGGGGCTCCCCCGGCGAAGAGG
                                                     C

AlaArgThrAspGlnMetGluValAspSerGlyProArgLysArgProLeuArgGlyGly
241     GCCCGAACGGACCAGATGGAGGTAGACTCCGGACCTAGGAAGAGGCCTCTCAGGGGAGGA

Arg
        PheThrAspLysGluArgGlnAspHisArgArgArgLysAlaLeuGluAsnLysLysLys
301     TTCACCGACAAGGAGAGGCAGGATCACCGACGAAGGAAGGCCCTCGAGAACAAGAAGAAG
                  G

GlnLeuSerAlaGlyGlyLysAsnLeuSerLysGluGluGluGluLeuArgArgLeu
361     CAGCTATCGGCGGGAGGCAAGAACCTCAGCAAGGAGGAAGAAGAGGAACTCAGGAGGTTG

Asn
        ThrGluGluAspGluArgArgGluArgArgValAlaGlyProProValGlyGlyValIle
421     ACCGAGGAAGACGAGAGAAGGGAAAGAAGAGTAGCCGGCCCGCCGGTTGGGGGTGTGATC
                                                                   A

Leu
        ProLeuGluGlyGlySerArgGlyAlaProGlyGlyGlyPheValProSerLeuGlnGly
481     CCCCTCGAAGGTGGATCGAGGGGAGCGCCCGGGGGCGGCTTCGTCCCCAGTCTGCAGGA
                                                                T

Gln
        ValProGluSerProPheSerArgThrGlyGluGlyLeuAspIleArgGlyAsnArgGly
541     GTCCCGGAGTCCCCCTTCTCTCGGACCGGGGAGGGGCTGGACATCAGGGGAAACCGGGGA
                                                                   A

END
        PheProTrpAspIleLeuPheProAlaAspProProPheSerProGlnSerCysArgPro
601     TTTCCATGGGATATACTCTTCCCAGCCGATCCGCCCTTTTCTCCCCAGAGTTGTCGACCC
                  A                  A
                  *

GlnEND
661     CAGTGA
```

FIG. 3

1   GTCCCCCTTCTCTCGGACCGGGGAGGGGCTGGACATCAGGGGAAACCGGGGATTTCCATG
    CAGGGGGAAGAGAGCCTGGCCCCTCCCCGACCTGTAGTCCCCTTTGGCCCCTAAAGGTAC

15 AVA2 SAU96, 18 HPA11 NCI1 SCRF1, 23 MNL1, 46 HPA11 NCI1 S
CRF1, 56 NC01, 57 NLA111,

61  GGATATACTCTTCCCAGCCGATCCACCCTTTTCTCCCCAGAGTTGTCGACCCCAGTGAAT
    CCTATATGAGAAGGGTCGGCTAGGTGGGAAAAGAGGGGTCTCAACAGCTGGGGTCACTTA

69 MB011, 80 BIN1 MB01, 105 ACC1 HINC11 SAL1, 106 TAQ1,

121 AAAGCGGGTTTCCACTCACAGGTTTGCGTCTCGCGTCCTTCTTTCCTCTTCGGGTCGGCA
    TTTCGCCCAAAGGTGAGTGTCCAAACGCAGAGCGCAGGAAGAAAGGAGAAGCCCAGCCGT

146 HGA1, 152 THA1, 153 HGA1, 165 MNL1, 167 MB011, 179 NLA11
1,

181 TGGCATCTCCACCTCCTCGCGGTCCGACCTGGGCATCCGAAGGAGGACGCACGTCCACTC
    ACCGTAGAGGTGGAGGAGCGCCAGGCTGGACCCGTAGGCTTCCTCCTGCGTGCAGGTGAG

183 SFAN1, 192 MNL1, 195 MNL1, 198 THA1, 201 AVA2 SAU96, 208
 ECOR11 SCRF1, 213 SFAN1, 214 FOK1, 223 MNL1, 226 HGA1, 231
MAE2, 235 BSTX1,

241 GGATGGCTAAGGGAGAGCCACTTTTCTCTCGATTCTCTATCGGAATCTAGAGAGATTTGT
    CCTACCGATTCCCTCTCGGTGAAAAGAGAGCTAAGAGATAGCCTTAGATCTCTCTAAACA

241 FOK1, 247 DDE1, 269 TAQ1, 271 HINF1, 283 HINF1, 286 XBA1
, 287 MAE1,

301 GGGTCCCATTCGCCATTACCGAGGGGACGGTCCCCTCGGAATGTTGCCCAGCCGGCGCCA
    CCCAGGGTAAGCGGTAATGGCTCCCCTGCCAGGGGAGCCTTACAACGGGTCGGCCGCGGT

301 NLA1V, 302 AVA2 NLA1V SAU96, 321 MNL1, 329 AVA2 NLA1V SA
U96, 334 MNL1, 346 BGL1, 351 NAE1, 352 HPA11, 354 AHA11 BAN1
 HAE11 NAR1 NLA1V, 355 HHA1,

361 GCGAGGAGGCTGGGACCATGCCGGCCATCAGGTAAGAAAGGATGGAACGCGGACCCTGCA
    CGCTCCTCCGACCCTGGTACGGCCGGTAGTCCATTCTTTCCTACCTTGCGCCTGGGACGT

363 MNL1, 366 MNL1, 372 NLA1V, 373 AVA2 SAU96, 377 NLA111, 3
80 NAE1, 381 HPA11, 382 CFR1, 383 HAE111, 400 FOK1, 408 THA1
, 411 AVA2 NLA1V SAU96, 416 PST1,

421 GAGTGGGGTCCCGCCATTCCTGGGCGACCCTTGGGGGGGGGAGTCGGAATCGAGCATCGG
    CTCACCCCAGGGCGGTAAGGACCCGCTGGGAACCCCCCCCCTCAGCCTTAGCTCGTAGCC

426 NLA1V, 427 AVA2 NLA1V SAU96, 439 ECOR11 SCRF1, 461 HINF1
, 467 HINF1, 470 TAQ1, 474 SFAN1,

481 GAGGGGCATCCCATGGCTCCACTGGTCCCCGGTGTTCCTAGCACCCCCTCCGGTCACTTT
    CTCCCCGTAGGGTACCGAGGTGACCAGGGGCCACAAGGATCGTGGGGGAGGCCAGTGAAA

481 MNL1, 486 SFAN1, 487 FOK1, 491 NC01, 492 NLA111, 495 NLA
1V, 504 AVA2 NLA1V SAU96, 508 NCI1 SCRF1, 509 HPA11, 518 MAE
1, 523 HGIE11, 527 MNL1, 530 HPA11, 533 MAE3, 539 ASU11, 540
 TAQ1,

541 CGAAGGGGGTCCGGGGTCCCGCTAGAT
    GCTTCCCCCAGGCCCCAGGGCGATCTA

547 NLA1V, 548 AVA2 SAU96, 551 HPA11 NCI1 SCRF1, 554 NLA1V,
555 AVA2 NLA1V SAU96, 562 MAE1,

| orf (READING FRAME) | | COORDINATES OF orf | COORDINATES OF EXPRESSED REGION |
|---|---|---|---|
| 1 | (2) | 539-1033 | 578-1014 |
| 2 | (1) | 786-1253 | 834-1253 |
| 5 | (1) | 1619-1014 | 1598-1014 |
| 6 | (3) | 1341-478 | 1110-485 |
| 7 | (1) | 506-63 | 481-63 |

HEPATITIS DELTA VIRUS P27$^\delta$ AND P24$^\delta$ VACCINE

CROSS-REFERENCE TO RELATED APPLICATION

This application is a divisional of application Ser. No. 08/262,667, filed Jun. 20, 1994, now abandoned, which is a continuation of application Ser. No. 08/097,519, filed Jul. 27, 1993, now U.S. Pat. No. 5,389,528, which is a continuation of application Ser. No. 07/932,920, filed Aug. 20, 1992, now abandoned, which is a continuation of application Ser. No. 07/765,917, filed Sep. 25, 1991, now abandoned, which is a divisional of application Ser. No. 07/053,991, filed May 22, 1987, now abandoned, which is a continuation-in-part of application Ser. No. 06/875,337, filed Jun. 17, 1986, now abandoned, from which applications priority is claimed pursuant to 35 USC §120.

TECHNICAL FIELD

The invention relates to materials and methodologies for managing the spread of hepatitis δ infection. More specifically, it relates to diagnostic DNA fragments, diagnostic proteins, and protective antigens and antibodies with respect to hepatitis δ virus.

BACKGROUND ART

An unusual form of hepatitis virus, hepatitis D (HDV), also called δ agent, warn discovered in 1977 by Rizztto, M., et al, *Gut* (1977) 18:997–1003. The virus was detected as a new antigen/antibody system by immunofluorescence in liver cells of patients infected with hepatitis B. Indeed, subsequent investigation showed that hepatitis D virus is dependent upon concomitant infection with hepatitis B in order to replicate. The nature of the helper function is not as yet understood. However, the HDV apparently contains a single-stranded a RNA genome surrounded by a "δ antigen" protein, which is in turn surrounded by hepatitis B surface antigen (HBsAg) in a 35–37 nm particulate configuration (Rizzetto, M. et al, *Proc Natl Acad Sci* USA (1980) 77:6124–6128; Bonino, F., et al, *Hepatology* (1981) 1:127–131). Thus, the DNA produced during infection will have a "genomic" strand and a complementary strand.

The epidemiology and mode of transmission appears to be similar for HDV to that of hepatitis B (HBV), in that it is transmitted through blood transfusion and by close direct contact of body fluids. Three patterns of HDV (or δ) infection have been identified: acute δ infection superimposed on chronic B, chronic δ superimposed on chronic B, and simultaneous acute δ and hepatitis B infections (Schiff, E. R., et al, *Diagnostic Medicine* (March 1985) 17–22). While the disease was originally identified in the Mediterranean basin, it appears to be spreading worldwide (Jacobson. I. M., et al, *Hepatology* (1985) 5:188–191). A review of the demographic and epidemiological aspects of this disease is also found in Rizzetto, M. et al, *J Hepatol* (1985) 1:187–193.

Although the course of the disease has been well characterized and the general structure of the virion is understood, no information has previously been available as to the genetic structure of the virus, nor has the nature of the δ antigen been characterized. The only available assay to detect the presence of the disease by using blood samples is an immunoassay marketed in Europe, which has not yet received FDA approval in the United States. Previous detection methods were limited to direct immunofluorescence in the nuclei of hepatocytes in biopsy specimens. One form of the assay is based on the ability of antibody in test serum to block binding of labeled IgG anti-δ to δ antigen per se. Another configuration relies on the ability of IgM anti-δ from the test serum to bind antihuman IgM (specific for μ chain) fixed to the solid phase, followed by the addition of standard δ antigen and labeled IgM anti-δ so that the presence of IgM anti-δ in the test serum (along with the added δ antigen) permits binding of labeled anti-δ IgM. Neither of these tests requires analysis of, or knowledge of, the δ antigen protein structure or HDV genomic structure.

It is now possible to design efficient probes for diagnosis of the disease by DNA hybridization, as well as to generate recombinant proteins usable as vaccines and as reagents in diagnostic testing. In addition, the recombinantly produced proteins can be used to generate antibodies useful for diagnosis or for passive therapy.

DISCLOSURE OF THE INVENTION

The invention provides a family of cDNA replicas of an entire HDV genomic sequence. Portions of these cDNA sequences are useful as probes to diagnose the presence of virus in clinical samples, and to isolate naturally occurring variants of the virus. An understanding of the basic genomic sequence (and its complement) also makes available the polypeptide sequence of the δ antigens encoded within one of the open reading frames and permits production of these peptides or portions thereof which are useful as standards or reagents in diagnostic tests and as components of vaccines. Similarly, analysis of other open reading frames in either strand permits deduction of additional viral peptide sequences which are characteristic of HDV and may be similarly useful. Protective antibodies may also be raised from the recombinantly produced proteins and may be obtained in polyclonal or monoclonal form.

The availability of an entire HDV sequence thus permits the design and construction of polypeptides which may either serve as vaccines or diagnostic reagents, or as intermediates in the production of monoclonal antibody (Mab) preparations useful in passive immunotherapy against the disease, or as intermediates in the production of antibodies useful as diagnostic reagents. Without the sequence of the entire genome at the disposal of the designer of therapeutic or preventive compositions, successful production of optimally effective products would be impossible.

Accordingly, in one aspect, the invention relates to nucleotide sequences useful for the production of HDV diagnostics and vaccines, derived from the HDV genome or its complement as represented in FIG. 2. The invention thus relates to utilizing this sequence or portions thereof as oligomeric probes, for production of peptides which can serve as diagnostic reagents or as vaccines, to these peptides themselves. and to polyclonal and monoclonal antibodies useful in diagnosis and treatment of the disease.

Other aspects of the invention include expression systems which are capable of effecting the production of a desired protein encoded by sequences derived from the complete genome, to recombinant vectors containing such systems or portions thereof, to recombinant host cells transformed with such vectors, to proteins produced by the transformed cells, and to vaccines prepared from such proteins. In addition, the invention relates to specific peptide sequences representing epitopes encoded by the genome, and to such sequences covalently linked to label or to carrier proteins. Carrier proteins, in addition to more conventional carriers, include the 22 nm particle associated with hepatitis B infection, which carries polyalbumin receptor sites, and is 1000-fold more immunogenic than the unassembled subunit component. By inserting antigenic HDV determinants into the 22 nm HBsAg particle, increased immunogenicity for these epitopes is obtained.

The invention also relates to the methods of preparing these desired polypeptide vaccines and immunoglobulins, and to kits for assay containing the probes, polypeptides, and/or immunoglobulins.

BRIEF DESCRIPTION OF THE DRAWINGS

FIG. 2 shows the complete nucleotide sequence of the double-stranded cDNA corresponding to the entire HDV RNA genome.

FIG. 3 shows the sequence of cDNA equivalent to the RNA of ORF5. The deduced amino acid sequence and heterogeneities in nucleotides as determined from other clones are also shown.

FIG. 4 shows the sequence of clone δ1 useful in obtaining the nucleotide sequence of the virus.

MODES OF CARRYING OUT THE INVENTION

A. Definitions

Figure 1:
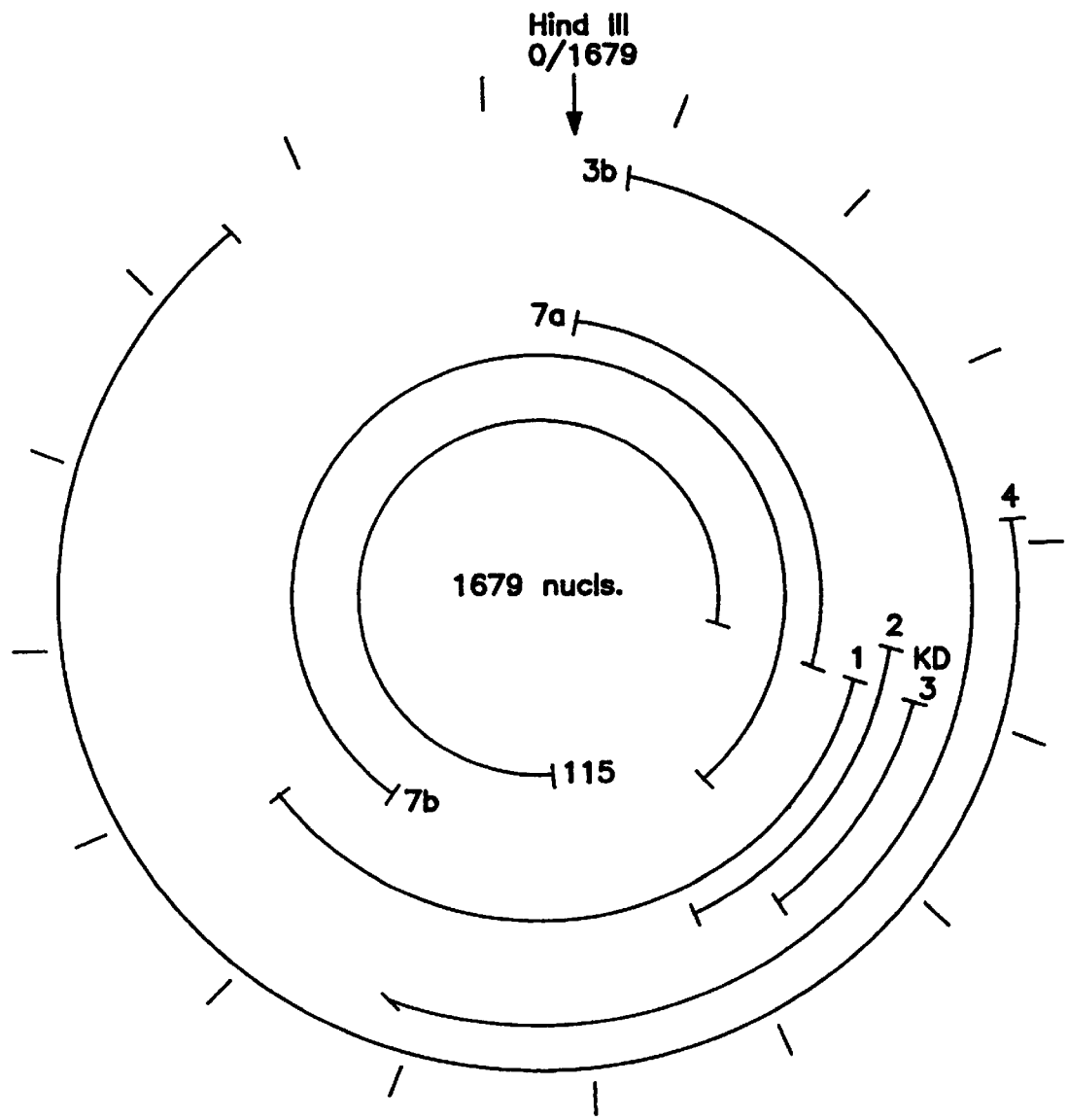
FIG. 1 shows a diagram of the HDV single-stranded RNA genome and the position of overlapping cDNA clones used to determine its structure.

As used herein, a nucleotide sequence "derived from" the HDV genome or CDNA refers to a sequence which retains the essential properties of the illustrated polynucleotide, representing a portion of the entire sequence from which it is derived, for the purpose intended. A specific, but nonlimiting, example of such derivation would be represented by a sequence which encodes an identical or substantially identical amino acid sequence, but, because of codon degeneracy, utilizes different specific codons; another example is the complementary strand. A probe or oligonucleotide useful in diagnostic tests needs to retain the complementarity of the sequence shown but may be shorter than the entire sequence or may skip over portions of it. However, for use in manipulation or expression, nucleotide changes are often desirable to create or delete restriction sites, provide processing sites, or to alter the encoded amino acid sequence in ways which do not adversely affect functionality. "Nucleotide sequence" refers both to a ribonucleotide and a deoxyribonucleotide sequence and includes both the genomic strand and its complementary strand.

A DNA "derived from" the nucleotide sequence which comprises the genome of HDV therefore refers to a DNA sequence which is comprised of a sequence corresponding to that of a region of the genomic nucleotide sequence (or its complement), or a combination of regions of that sequence modified in ways known in the art to be consistent with its intended use. These DNAs are, of course, not necessarily physically derived from the nucleotide sequence of the gene, but refer to polynucleotides generated in whatever manner which are based on the information provided by the sequence of bases in the region(s) from which the polynucleotide is derived. For example, regions from which typical DNA sequences can be "derived" include regions encoding specific epitopes and regions encoding portions of δ antigen. Similarly a peptide "derived from" the δ antigens refers to an amino acid sequence substantially identical to that of these polypeptides or a portion thereof, having the same biological properties as that portion. The manner of synthesis of such a "derived" peptide is not material—it may be chemical synthesis or recombinant means, for example.

"Recombinant host cells", "host cells", "cells", "cell lines", "cell cultures", and other such terms denoting microorganisms or higher eukaryotic cell lines cultured as unicellular entities, are used interchangeably, and refer to cells which can be, or have been, used as recipients for recombinant vector or other transfer DNA, and include the progeny of the original cell transfected. It is understood that the progeny of a single parental cell may not necessarily be completely identical in morphology or in genomic or total DNA complement as the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

"Control sequence" refers to DNA sequences which are necessary to effect the expression of coding sequences to which they are ligated. The nature of such control sequences differs depending on the host organism: in prokaryotes, generally such control sequences include promoter and ribosome binding site: in eukaryotes, generally, such control sequences include promoters, terminators, and, in some instances, enhancers. The term "control sequences" is intended to include, at a minimum, all components whose presence is necessary for expression, and may also include additional components whose presence is advantageous.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" is a region of a polynucleotide sequence which encodes for a polypeptide.

"Immunologically identifiable with/as" refers to the presence of epitopes in the non-native, i.e., artificially synthesized or recombinant protein, which is also present in HDV viral proteins. These epitopes may be identified by their immunological reactivity with antibodies directed against the HDV proteins. Their presence in the non-native protein may be detected by direct reactivity with the HDV antibodies, as well as by competition assays between the non-native proteins and HDV proteins for antibodies to HDV proteins. Methods of detecting antibody binding and of determining competition in binding are known to those of average skill in the art, and are also illustrated infra.

B. General Description

The useful materials and processes of the present invention are made possible by the provision of a family of nucleotide sequences each containing an entire genome of hepatitis D virus. The availability of this family of polynucleotides, first, permits the isolation of other members of the genome family which differ by small heterogeneities. Second, it permits the construction of DNA and proteins useful in diagnosis with respect to DNA, oligomers of about 8–10 bp or more useful as hybridization probes in disease diagnosis. Such probes may be used to detect the presence of the viral genome in, for example, sera of subjects suspected of harboring the virus. The HDV sequences also allow the design and production of HDV-specific polypeptides which are useful as diagnostic reagents for the presence of antibodies raised by HDV in serum or blood. Antibodies raised against these polypeptides are also useful as diagnostics. (Because open reading frames in addition to that for δ antigen can be deciphered in the context of the complete genome or its complement. the primary structures of HDV-related proteins, other than δ antigen per se, can be deduced. These may also be marker polypeptides, characteristic of the virus, and useful in diagnosis and, possibly, in immunization.) Finally, knowledge of the gene sequences also enables the design and production of vaccines effective against HDV and also production of protective antibodies.

Sequencing information available from the genome allows the amino acid sequence of the δ antigen or other polypeptides to be deduced and suitable epitopes identified. The entire δ antigen or suitable portions thereof can be produced by fragments of the relevant DNA which are obtained and expressed independently, thus providing desired polypeptides using recombinant techniques. Both prokaryotic and eukaryotic hosts are useful for such expression. Short polypeptide fragments may also be chemically synthesized and linked to carrier proteins for use as vaccines. In addition, the epitopes may be produced linked to a protein conferring immunogenicity. The proteins thus produced may themselves be used as vaccines, or may be used to induce immunocompetent B cells in hosts, which B cells can then be used to produce hybridomas that secrete antibodies useful in passive immunotherapy.

B.1. Preparation of the HDV Gene Sequence

The serum of chimpanzees infected with HDV and containing a high titer of the virus (about $10^{11}$ chimp infectious disease dose/ml) was used as the source of the virus. Nucleic acid extracted from the harvested virus, when analyzed by denaturing gel electrophoresis, consistently yielded a doublet RNA containing about 1700 nucleotides. Using this RNA as a template, an approximately 164 bp cDNA clone, pkD3, which specifically hybridizes to the RNA doublet, was obtained, and its DNA sequence determined (Denniston, K. J., et al, *Science* (1986) 232:873–975). Based on this determined DNA sequence, provided in advance of publication, two complementary synthetic oligomers were prepared, only one of which hybridizes to the doublet RNA.

The hybridizing oligomer was then used to probe a cDNA library that was prepared according to the Okayama/Berg method from the doublet RNA, resulting in clone δ1, containing a 570 bp insert, which hybridized to the RNA doublet and was used as a probe to obtain overlapping clone δ2 from the same library.

Additional clones δ4 and δ115 were obtained by probing with the δ1 clone a cDNA library prepared in pBR322 using random priming of the isolated RNA, δ115 was then used as a probe to obtain overlapping clones δ7a, δ3b, and δ7b, The independent clones δ3, δ4, δ7a, δ7b, and δ115, along with δ1 and δ2 provided the complete sequence of the circular single-stranded 1679 nucleotide RNA diagrammed in FIG. 1.

The description of the method to retrieve the entire HDV genome is, of course, mostly of historical interest. The resultant sequence (and therefore, also, its complement) is provided herein, and the entire sequence, or any portion thereof, could also be prepared using synthetic methods, or by a combination of synthetic methods with retrieval of partial sequences using methods similar to those here described.

B.2. Preparation of Viral Polypeptides and Their Fragments

The availability of the entire genomic sequences permits construction of expression vectors encoding antigenically active regions of the δ antigen, and any other viral polypeptide encoded by the genome or its complement. Fragments encoding the desired proteins are obtained from the cDNA clones using conventional restriction digestion or by synthetic methods and are ligated into vectors, for example, containing portions of fusion sequences such as β-galactosidase or superoxide dismutase (SOD), preferably SOD, Any desired portion of the HDV genome containing an open reading frame, in either sense strand, can be obtained as a recombinant protein, such as a mature or fusion protein, or can be provided by chemical synthesis or general recombinant means.

The DNA encoding the desired polypeptide. whether in fused or mature form, and whether or not containing a signal sequence to permit secretion, may be ligated into expression vectors suitable for any convenient host. Both eukaryotic and prokaryotic host systems are presently used in forming recombinant polypeptides, and a summary of some of the more common control systems and host cell lines is given in section C.1 herein below. The polypeptide is then purified from lysed cells or from the culture medium and purified to the extent needed for its intended use. Such peptides can be used as diagnostics or formulated into vaccines, Antibodies raised against these polypeptides can also be used as diagnostics.

Analysis of the genome shows the presence of a number of open reading frames (ORFs), at least one of which, ORF5, encodes the δ antigen. Others may encode previously unknown viral polypeptides. Several such frames containing a minimum of about 150 nucleotides preceded by an ATG start codon were identified. Additional reading frames are present with longer open sequences, but without ATG start codons. The reading frames were found both in the cDNA strand having the same sense as the genome, and in the antigenome strand, Five of the large ORFs encoding polypeptides containing a methionine proximal to the amino terminus were expressed in bacteria. Only polypeptides encoded by the antigenomic ORF5 cross-reacted with antisera obtained from patients with hepatitis δ infections, Based upon immunological analyses using viral extracts and recombinant ORF polypeptides synthesized in bacteria and yeast, ORF5 encodes the immunogenic epitopes shared by both hepatitis δ viral polypeptides p27$^δ$ and p24$^δ$, and probably represents the complete structural gene for p27$^δ$ and p24$^δ$. Based upon immunocompetition studies described herein, the nuclear hepatitis δ antigen is comprised of both p27$^δ$ and p24$^δ$.

A comparison of cDNA nucleotides sequences in clones 115, 7a, 1, 4, 2, 7b, and 3b showed that there is a small degree of heterogeneity in the overlapping sequences (see Table 2), Nucleotide sequence heterogeneity is not unusual in RNA containing viruses, Holland, J., et al (1982) *Science* 215:1577. The sequence heterogeneities at portion 608 of ORF5 in particular may be the basis for the distinction between p27$^δ$ and p24$^δ$, i.e., the size of the two polypeptides may result from the additional amino acids in the C-terminal portion of p27$^δ$. If the position is occupied by G, the triplet containing it encodes tryptophan, and translation continues until the opal stop codon beginning at position 664 (see FIG. 3). Alternatively, if position 608 contains A, the triplet containing it encodes an amber stop codon, and translation ceases at this point unless the last cell has the ability to suppress the amber codon, thereby allowing translation to continue to the opal codon.

B.3. Preparation of Antigenic Polypeptides and Conjugation with Carrier

The antigenic region of peptides is generally relatively small—typically 10 amino acids or less in length. Fragments of as few as 5 amino acids may typically characterize an antigenic region. These segments may correspond to regions of δ antigen or to regions of additional encoded marker polypeptides. Accordingly, using the genome of HDV as a basis, DNAs encoding short segments of peptides can be expressed recombinantly either as fusion proteins or as isolated peptides. In addition, short amino acid sequences can be chemically synthesized conveniently. In instances wherein the synthesized peptide is correctly configured so as to provide the correct epitope, but too small to be immunogenic, the peptide may be linked to a suitable carrier.

A number of techniques for obtaining such linkage are known in the art, including the formation of disulfide linkages using N-succinimidyl-3-(2-pyridylthio)propionate (SPDP) and succinimidyl 4-(N-maleimido-methyl) cyclohexane-1-carboxylate (SMCC) obtained from Pierce Company, Rockford, Ill. (If the peptide lacks a sulfhydryl, this can be provided by addition of a cysteine residue.) These reagents create a disulfide linkage between themselves and peptide cysteine residues on one protein and an amide linkage through the ε-amino on a lysine, or other free amino group in the other. A variety of such disulfide/amide-forming agents are known. See, for example, *Immun Rev* (1982) 62:185. Other bifunctional coupling agents form a thioether rather than a disulfide linkage. Many of these thioether-forming agents are commercially available and include reactive esters of 6-maleimidocaproic acid, 2-bromoacetic acid, 2-iodoacetic acid, 4-(N-maleimido-methyl) cyclohexane-1-carboxylic acid, and the like. The carboxyl groups can be activated by combining them with succinimide or 1-hydroxy-2-nitro-4-sulfonic acid, sodium salt. The foregoing list is not meant to exhaustive, and modifications of the named compounds can clearly be used.

Any carrier may be used, which does not itself induce the production of antibodies harmful to the host, such as the various serum albumins, tetanus toxoids, or keyhole limpet hemocyanin (KLH).

The conjugates, when injected into suitable subjects, will result in the production of antisera which contain immunoglobulins specifically reactive against not only the conjugates, but also against fusion proteins carrying the analogous portions of the sequence, and against appropriate determinants within whole HDV.

B.4. Preparation of Hybrid Particle Immunogens Containing HDV Epitopes

The immunogenicity of the epitotes of HDV may also be enhanced by preparing them in mammalian or yeast systems fused with particle-forming proteins such as that associated with hepatitis B surface antigen. Constructs wherein the HDV epitope is linked directly to the particle-forming protein coding sequences produce hybrids which are immunogenic with respect to the HDV epitope. In addition, all of the vectors prepared include epitopes specific to hepatitis B virus (HBV), having various degrees of immunogenicity, such as, for example, the pre-S peptide. Thus, particles constructed from particle-forming protein which include HDV sequences are immunogenic with respect to both HDV and HBV.

Hepatitis surface antigen (HBsAg) has been shown to be formed and assembled in *S. cerevisiae* (Valenzuela et al, *Nature* (1982) 298:344–350), as well as in, for example, mammalian cells (Valenzuela. P., et al, *Hepatitis B* (1984), Millman, I., et al, ed, Plenum Press. pp. 225–236). The formation of such particles has been shown to enhance the immunogenicity of the monomer subunit. The constructs may also include the immunodominant epitope of HBsAg, comprising-the 55 amino acids of the presurface (pre-S) region, (Neurath et al, *Science* (1984) 224:392–394.) Constructs of the pre-S-HBsAg particle expressible in yeast are disclosed in U.S. Ser. No. 621,756, filed Jun. 18, 1984; hybrids including heterologous viral sequences for yeast expression are disclosed in U.S. Ser. No. 650,323, filed Sep. 13, 1984. Both applications are assigned to the herein assignee and incorporated by reference. These constructs may also be expressed in mammalian cells such as Chinese hamster ovary cells using an SV40-dihydrotolate reductase vector (Michelle et al, *Int Symp on Viral Hepatitis* (1984)).

In addition, portions of the particle-forming protein coding sequence per se may be replaced with codons for an HDV epitope. In this replacement, regions which are not required to mediate the aggregation of units to form immunogenic particles in yeast or mammals can be deleted, thus eliminating additional hepatitis B antigenic sites from competition with the HDV epitope.

B.5. Preparation of Vaccines

Preparation of vaccines which contain peptide sequences as active ingredients is also well understood in the art. Typically, such vaccines are prepared as injectables, either as liquid solutions or suspensions: solid forms suitable for solution in, or suspension in, liquid prior to injection may also be prepared. The preparation may also be emulsified or the protein encapsulated in liposomes. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccine. The vaccines are conventionally administered parenterally, by injection, for example, either subcutaneously or intramuscularly. Additional formulations which are suitable for other nodes of administration include suppositories and, in some cases, oral formulations. For suppositories, traditional binders and carriers may include, for example, polyalkaline glycols or triglycerides; such suppositories may be formed from mixtures containing the active ingredient in the range of 0.5% to 10%. preferably 1%–2%. Oral formulations include such normally employed excipients as, for example, pharmaceutical grades of mannitol, lactose, starch magnesium stearate, sodium saccharine cellulose, magnesium carbonate and the like. These compositions take the form of solutions, suspensions, tablets, pills, capsules, sustained release formulations or powders and contain 10%–95% of active ingredient, preferably 25%–70%.

The proteins may be formulated into the vaccine as neutral or salt forms. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a wanner compatible with the dosage formulation, and in such amount as will be therapeutically effective and immunogenic. The quantity to be administered depends on the subject to be treated, capacity of the subject's immune system to synthesize antibodies, and the degree of protection desired. Precise amounts of active ingredient required to be administered depend on the judgment of the practitioner and are peculiar to each subject. It should be noted that since $\delta$ infection is dependent on infection with hepatitis B, a subpopulation for which an anti-$\delta$ vaccine is particularly useful is the pool of hepatitis B carriers. It may also be beneficial to construct "dual " vaccines containing both B and D antigens.

The polypeptides encoded within ORF5 (and peptides derived therefrom) are particularly suitable vaccine components for protection against HDV infection, despite the fact that ORF5 encodes core antigens of the HDV particle. Vaccines containing recombinantly produced core antigens of HBV are effective in protecting against or alleviating hepatitis B infection, Murray. K., et al, EMBO J (1984) 3:645.

B.6. Preparation of Antibodies Against HDV Epitopes

The immunogenic proteins prepared as described above are used to immunize mammals. The resulting antisera are useful as diagnostic reagents. Also lymphocytes or splenocytes from these animals may be used to prepare hybridomas capable of secreting monoclonal antibodies directed against these epitopes and cross-reactive against the infective virus. The resulting monoclonal antibodies are particularly useful in diagnosis, and those which are neutralizing are useful in passive immunotherapy.

The polypeptides encoded within ORF5, and antibodies to these polypeptides are particularly useful for immunodiagnosis of HDV. As discussed below, ORF5 encodes the δ antigen, which apparently is comprised of two viral polypeptides, $p24^{\delta}$ and $p27^{\delta}$.

B.7. Diagnostic Oligonucleotide Probes and Kits

Using the disclosed family of HDV genomes as a basis, oligomers of approximately 8 bp or more can be prepared, either by excision or synthetically, which hybridize with the HDV genome and are useful in detection of the virus in diseased individuals. While 8 bp is a workable length, sequences of 10–12 bp are preferred, and about 20 bp appears optimal. Preferably these sequences will derive from regions which lack the heterogeneity. These probes can be prepared using routine methods, including automated oligonucleotide synthetic methods. Among useful probes, for example, are the clone δ1, the various oligomers useful in probing cDNA libraries set forth below, and the additional clones disclosed herein. Particularly useful are those clones containing fragments of ORF5. Any portion of the genome or its complement will be satisfactory. For use as probes, complete complementarity is desirable, though it may be unnecessary as the length of the fragment is increased.

For use of such probes as diagnostics, the biological sample to be analyzed, such as blood or serum, is treated, if desired, to extract the nucleic acids contained therein, and the resulting nucleic acid subjected to gel electrophoresis or other size separation technique or simply dot blotted without size separation. The probes are then labeled, using, for example, nick translation or kinasing, and the extracted nucleic acids then treated with labeled probe under suitable hybridization stringencies.

Since the probes can be made completely complementary to the viral RNA, high stringency conditions are desirable in order to prevent false positives. However, high stringency conditions should only be used if the probes are complementary to regions of the viral genome which lack heterogeneity. The stringency of hybridization is determined by a number of actors, including temperature, ionic strength, length of time permitted for hybridization and for washing, and concentration of formamide. These factors are outlined, for example, in Maniatis, T., et al, *Molecular Cloning: A Laboratory Manual* (1982). Cold Spring Harbor Press, Cold Spring Harbor, N.Y. Increased stringency can be achieved, for example, by raising the temperature, shortening the time of exposure, and adjusting the ionic strength.

The probes can be packaged into diagnostic kits which include the labeled DNA, suitably packaged, additional reagents, and materials needed for the particular protocol, and instructions for conducting the test.

B.8. Immunoassay Diagnostic Kits

Both the polypeptides which react immunologically with serum containing HDV antibodies, e.g., the ORF5-encoded polypeptides, and the antibodies raised against these polypeptides are useful as components of diagnostic kits designed to detect the presence of HDV antibodies in blood or serum samples or to detect the presence of the virus, as the case may be. Design of the immunoassays is subject to a great deal of variation, and several protocols based on competition or direct reaction on solid supports or on immunoprecipitation, for example, are available. Most assays involve the use of labeled antibody or polypeptide containing fluorescent, radioactive or dye molecules as tags. Enzyme-labeled and mediated immunoassays are also commonly used. Therefore, kits suitable for use in such protocols and containing the appropriate labeled reagents are constructed by packaging the appropriate materials, including the antibodies or polypeptides of the invention in suitable containers along with the remaining requirements for conduct of the assay and a suitable set of instructions for conducting it.

C. General Methods

The general techniques used in extracting RNA from the virus, preparing and probing a cDNA library, sequencing clones, constructing expression vectors, transforming cells, and the like are known in the art and laboratory manuals are available describing these techniques. However, as a general guide, the following sets forth some sources currently available for such procedures, and for materials useful in carrying them out.

C.1. Hosts and Expression Control Sequences

Both prokaryotic and eukaryotic host cells may be used for expression of desired coding sequences when appropriate control sequences used are compatible with the designated host. Among prokaryotic hosts, *E. coli* is most frequently used, mostly for convenience. Expression control sequences for prokaryotes include promoters, optionally containing operator portions, and ribosome binding sites. Transfer vectors compatible with prokaryotic hosts are commonly derived from, for example, pBR322 a plasmid containing operons conferring ampicillin and tetracycline resistance, and the various pUC vectors, which also contain sequences conferring antibiotic resistance. The foregoing operons may be used as markers to obtain successful transformants by selection. Commonly used prokaryotic control sequences include the B lactamase (penicillinase) and lactose promoter systems (Chang, et al, *Nature* (1977) 198:1056), the tryptophan (trp) promoter system (Goeddel, et al, *Nucleic Acids Res* (1980) 8:4057) and the λ derived $P_L$ promoter and N gene ribosome binding site (Shimatake et al, *Nature* (1981) 292:128) and the hybrid tac promoter (De Boer et al, *Proc Natl Acad Sci* (*USA*) (1983) 80:21–25) derived from sequences of the trp and the lac UV5 promoters. The foregoing systems are particularly compatible with *E. coli*; if desired other prokaryotic hosts such as strains of Bacillus or Pseudomonas may be used, with corresponding control sequences.

Eukaryotic hosts include yeast and mammalian cell culture. *Saccharomyces cerevisiae*, or Baker's yeast and *Saccharomyces carlsbergensis* are the most commonly used yeast hosts, again because of convenience. Yeast compatible vectors carry markers which permit selection of successful transformants by conferring prototrophy to auxotrophic mutants or by conferring antibiotic resistance or resistance to heavy metals on wild-type strains. Yeast compatible vectors may employ the 2 micron origin of replication (Broach, J., et al, *Meth Enz* (1983) 101:307) the combination of CEN3 and ARS1 or other means for assuring replication, such as sequences which will result in incorporation of an appropriate fragment into the host cell genome. Control sequences for yeast vectors include promoters for the synthesis for glycolytic enzymes (Hess et al, *J Adv Enzyme Reg* (1968) 7:149. Holland et al, *Biochemistry* (1978) 17:4900), and the promoter for 3 phosphoglycerate kinase (Hitzeman et al, *J Biol Chem* (1980) 255:2073). For yeast expression, terminators may also be included, such as those derived from the enolase gene (Holland, M. J., *J Biol Chem* (1981) 256:1385). Particularly useful control systems include those specifically described herein, which comprise the glyceraldehyde-3 phosphate dehydrogenase (GAPDH) promoter or alcohol dehydrogenase (ADH) regulatable promoter, terminators also derived from GAPDH, and, it secretion is desired, leader sequence from yeast alpha factor. These systems are described in detail in U.S. Ser. No. 468,589 and 522,909, filed Feb. 22, 1983 and Aug. 12, 1983, respectively, both assigned to the herein assignee, and incorporated herein by reference.

Mammalian cell lines available as hosts for expression include many immortalized cell lines available from the American Type Culture Collection, including HeLa cells, Chinese hamster ovary (CHO) cells, baby hamster kidney (BHK) cells, and a number of other cell lines. Suitable promoters for mammalian cells prominently include viral promoters such as that from Simian virus 40 (SV40) (Fiers, et al, *Nature* (1978) 273:113) or other viral promoters such as the Rous sarcoma virus (RSV) adenovirus, and bovine papilloma virus (BPV). Mammalian cells may also require terminator sequences. Vectors suitable for replication in mammalian cells may include viral replicons, or sequences which insure integration of the appropriate sequences into the host genome.

C.2. Transformations

The transformation procedure used depends on the host to be transformed, Bacterial transformation generally employs treatment with calcium or rubidium chloride (Cohen, S. N., *Proc Natl Acad Sci* (USA) (1972) 69:2110, Maniatis et al, *Molecular Cloning: A Laboratory Manual* (1982) Cold Spring Harbor Press, page 254). Yeast transformations may be carried out using the method of Hinnen et al, *Proc Natl Acad Sci* (1978) 75:1929–1933. Mammalian transformations are conducted using the calcium phosphate precipitation method of Graham and van der Eb, *Virology* (1978) 52:546, or the various modifications thereof.

C.3. Vector Construction

Vector construction employs techniques which are by now quite well understood. Site-specific DNA cleavage is performed by treating with suitable restriction enzymes under conditions which generally are specified by the manufacturer of these commercially available enzymes (see, e.g., The New England Biolabs Product Catalog). In general, about 1 µg of plasmid or DNA sequence is cleaved by 1 unit enzyme in about 20 µl buffer solution for an incubation time of about 1–2 hr at about 37° C. After incubation with the restriction enzyme, protein is removed by phenol/chloroform extraction and the DNA recovered by reprecipitation with ethanol. The cleaved fragments may be separated using polyacrylamide or agarose gel electrophoresis techniques, according to the general procedures found in *Methods in Enzymology* (1980) 65:499–560.

Sticky ended cleavage fragments may be blunt ended using *E. coli* DNA polymerase I (Klenow) in the presence of the appropriate deoxynucleotide triphosphates (dNTPs) using incubation conditions appropriate to the polymerase. The polymerase digests protruding 3' single strands, but fills in 5' protruding ends, according to the dNTPs present in the mixture. Treatment with S1 nuclease may also be used, as this results in hydrolysis of any single stranded DNA portion.

Ligations are carried out using standard buffer and temperature conditions using T4 DNA ligase, and ATP; sticky end ligations require less ATP and less ligase than blunt end ligations. When vector fragments are used as part of a ligation mixture, the vector fragment is often treated with bacterial alkaline phosphatase (BAP) in order to remove the 5' phosphate and thus prevent religation of the vector; alternatively, restriction enzyme digestion of unwanted fragments can be used to prevent religation.

Ligation mixtures are transformed into suitable cloning hosts, such as *E. coli*, and successful transformants selected by, for example, antibiotic resistance, and screened for the correct construction.

C.4. Construction of Desired DNA Sequences

Synthetic oligonucleotides may be prepared using an automated oligonucleotide synthesizer as described by Warner, B. D., et al, *DNA* (1984)3:401–411. If desired, these synthetic strands may be kinased for labeling with $^{32}P$ by using an excess of polynucleotide kinase in the presence of labeled ATP, under standard kinasing conditions.

DNA sequences including those isolated from genomic or cDNA libraries may be modified by site directed mutagenesis, as described by Zoller, M., et al, *Nucleic Acids Res* (1982) 10:6487–6499. Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. The resulting double stranded DNA is transformed into a phage supporting host bacterium, and cultures of the transformed bacteria, which will contain replications of each strand of the phage, are plated in agar to obtain plaques, Theoretically 50% of the new plaques will contain phage having as a single strand the mutated form: 50% will have the original sequence. Replicates of the plaques are hybridized to kinased synthetic probe at temperatures and conditions which permit hybridization with the correct strand, but not with the unmodified sequence. The thus identified, desired, modified sequences are then recovered and cloned to serve as sources for the desired DNA.

C.5. Hybridization with Probe

DNA libraries are probed using the procedure of Grunstein and Hogness (*Proc Natl Acad Sci* (USA) (1975) 73:3961). Briefly, in this procedure, the DNA to be probed is immobilized on nitrocellulose filters, denatured, and prehybridized with a buffer containing 0–50% formamide, 0.6M NaCl. 60 mM sodium citrate, 0.02% (wt/v) each of bovine serum albumin, polyvinyl pyrollidine, and Ficoll, 50 mM sodium phosphate (pH 6.5), 1% glycine, and 100 $\mu$g/ml carrier denatured DNA. The percentage of formamide in the buffer, as well as the time and temperature conditions of the prehybridization and subsequent hybridization steps depends on the stringency desired. Oligomeric probes which require lower stringency conditions are generally used with low percentages of formamide, lower temperatures, and longer hybridization times. Probes containing more than 30 or 40 nucleotides such as those derived from cDNA or genomic sequences generally employ higher temperatures, e.g. about 40–42° and a high percentage, e.g. 50% formamide. Following prehybridization this same buffer, now containing the $^{32}P$ kinased oligonucleotide probe, is added to obtain hybridization. Radioautography of the treated filters shows the location of the hybridized probe, and the corresponding locations on replica filters which have not been probed can then be used as the source of the desired DNA.

C.6. Verification of Construction and Sequencing

For routine vector constructions, ligation mixtures are transformed into *E. coli* strain HB101 or other suitable host, and successful transformants selected by antibiotic resistance or other markers. Plasmids from the transformants are then prepared according to the method of Clewell. D. B., et al, *Proc Natl Acad Sci* (USA) (1969) 62:1159, usually following chloramphenicol amplification (Clewell, D. B., *J Bacteriol* (1972) 110:667). The isolated DNA is isolated and analyzed by restriction analysis. or sequenced by the dideoxy method of Sanger, F., et al, *Proc Natl Acad Sci* (USA) (1977) 74:5463, as further described by Messing, et al, *Nucleic Acids Res* (1981) 9:309, or by the method of Maxam et al, *Methods in Enzymology* (1980) 65:499. To overcome problems with band compression, which are sometimes observed in GC rich regions. T-deazoguanosine was used. Barr. P., et al *Biotechniques* (1986) 4:428.

D. Examples

The following examples are intended to illustrate but not to limit the invention. The procedures set forth, for example, in ¶D.1 may, if desired, be repeated but need not be, as techniques are available for construction of the desired nucleotide sequences based on the information provided by the invention. Expression is exemplified in *E. coli* and yeast; however, other systems are available as set forth more fully in ¶C.1. Additional epitopes derived from the genomic structure may also be produced, and used to generate antibodies as set forth below.

D.1. Preparation of HDV cDNA

Chimpanzee serum containing approximately $10^{11}$ chimp infectious doses/ml of δ agent was ultracentrifuged and the nucleic acid was extracted from the resulting pellet after incubation with proteinase K. Briefly, the RNA was extracted from the virions by conventional procedures, for example, that disclosed by Ticehurst, J. E., et al, *Proc Acad Sci* (USA) (1983) 80:5885–5889, including protease treatment and phenol/chloroform extraction, followed by ethanol precipitation. HDV was centrifuged through 20% sucrose in 20 mM HEPES pH 7.5 and 0.1% BSA. After proteolytic digestion with 1 mg/ml proteinase k, 50 $\mu$g/ml yeast transfer RNA, 20 mM HEPES pH 7.5, 50 mM EDTA, 200 mM NaCl and 1% SDS overnight at 37° C. RNA was purified by phenol/CHCl$_3$ extraction and precipitation with ethanol.

The nucleic acid was analyzed using denaturing gel electrophoresis to obtain a 1700 nucleotide RNA doublet as determined by hybridization analysis. The doublet was used by Denniston. K. J., et al, *Science* (1986) (supra), to obtain an approximately 164 bp cDNA clone, pkD3, which specifically hybridizes to the doublet, as well as to samples infected with δ agent.

Two complementary oligonucleotides were synthesized using the sequence information obtained from the Denniston et al pkD3 cDNA clone as a basis. Probe 1: 5'-GATGCCCTTCCCGATGCTCGATTCCGACTC and Probe 2: 5'-GAGTCGGAATCGAGCATCGGGAAGGGCATC were labeled by kinasing using 200 $\mu$Ci $^{32}$[P] ATP, >5 Ci/$\mu$mol. Probes were kinased at the 5' terminus with T4 kinase according to the method of Lillehaug, et al, *Biochemistry* (1976) 15:1858 followed by purification on a Sep-pak C18 cartridge (Millipore) using elution with 50% v/v CH$_3$OH, 50 mM ammonium acetate, pH 7.5.

For hybridization to DNA probes, HDV RNA was electrophoresed through a 1% agarose-formaldehyde gel along with control chimpanzee RNA and DNA size markers (Lehrach, H., et al, *Biochemistry* (1977) 16:4743). Each gel was blotted onto a nitrocellulose membrane and hybridized to labeled specific probe as described by Thomas, *Proc Natl Acad Sci* (USA) (1980) 77:5201. Treatment of gels containing the template RNA and suitable controls with each of these probes showed that only Probe 2 hybridized to the template confirming the single stranded nature of the genome.

A cDNA library was prepared from the original RNA extract of the chimpanzee serum pellet by the method of Okayama and Berg (*Mol Cell Biol* (1982) 2:161–170). after attaching poly(rA) tails to the 3'-hydroxy terminus of the RNA. The RNA showed extensive degradation during the incubation with the poly(rA) polymerase. However, probing the resulting cDNA library with Probe 2 resulted in the retrieval of a clone, δ1, which has the sequence shown in FIG. 4. A smaller (250 bp) overlapping clone, δ2, was also found in this library using a 435 bp NcoI fragment excised from the cloned cDNA of δ1.

Strand-specific probes were prepared from δ1 using a ~950 bp PvuII/HindII restriction fragment (containing flanking regions) or a ~450 bp PvuII/PstI fragments, in order to identify the genomic and complementary strands of the cDNA. These fragments were ligated into M13 vectors to generate complementing single-stranded δ templates. To prepare hybridization probes, 0.8 μg of each template DNA was mixed with 0.1 μg of hybridization probe primer (New England Biolabs) in 200 μM NaCl, followed by incubation for 15 minutes at 37° C. after denaturing in a boiling water bath for 1 minute. The annealed mixture was incubated for 2 hours at 15° C. and 200 μl containing 50 mM Tris-Cl. pH 7.5, 5 mM MgCl$_2$,10 mM β-mercaptoethanol, 50 μg/ml BSA, 0.1 mM dATP, dGTP, and dTTP, 14 μM dCTP (1000 Ci/mmol). along with 250 U/ml Klenow to label the single-stranded inserts. The reaction was stopped and the DNA purified on G50 Sephadex and the resulting probe eluting in void volume, was used to hybridize to a Northern blot containing the labeled template RNA.

Figure 5:
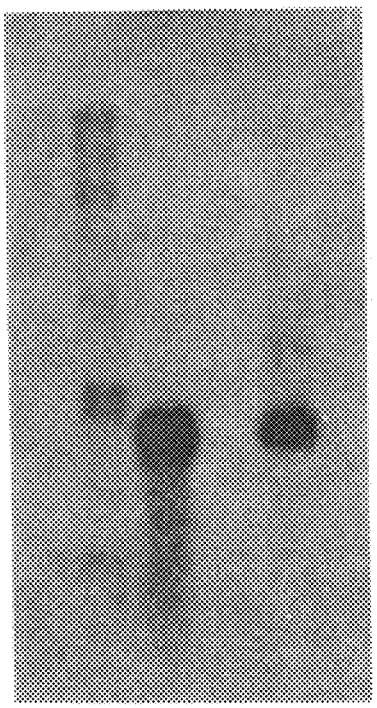
FIG. 5 shows the hybridization of probe to viral RNA.
Figure 6A:
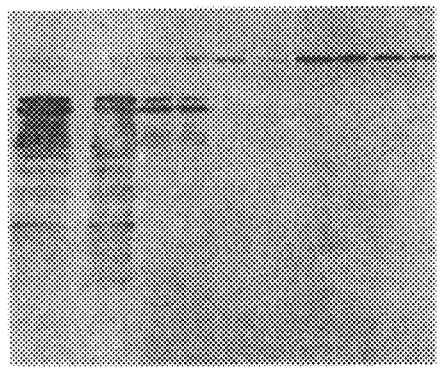
FIG. 6 shows gels demonstrating the production by *E. coli* of immunologically reactive HDV peptides.
Figure 6B:
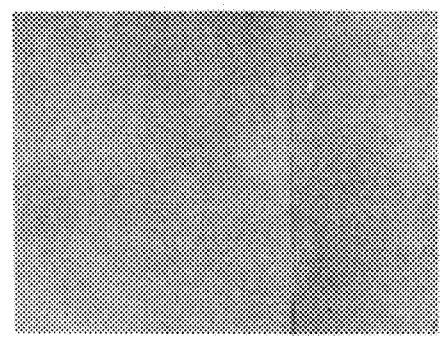

The results for a successful probe (one of the ~450 bp PvuI/PstI fragment strands) are shown in FIG. 5. Lane 1 contains labeled markers, lane 2 contains 10 ng δ virion RNA from plasma; lanes 3 and 4 contain 1.4 μg of liver RNA from control and infected chimpanzees, respectively. Lanes 2 and 4 clearly show the presence of viral nucleic acid.

An additional HDV cDNA library was prepared by using calf thymus random primers (Taylor, J. M., et al, *Biochem Biophys Acta* (1976) 442:324–3300) to prime reverse transcription of HDV RNA. The resulting single-stranded cDNA was then purified and rendered double-stranded by incubation with *E. coli* DNA polymerase I. Following treatment with S1 nuclease, the cDNA was tailed with oligo-dC using terminal transferase and annealed with dG-tailed pBR322 that had been previously restricted with PstI. The plasmids were then transformed into the host bacterium *E. coli* MC1061, and tetracycline-resistant recombinants were colony-hybridized as described below to screen for δ clones. (These general methods are described in Maniatis, T., et al, in *Molecular Cloning* (Cold Spring Harbor Laboratory) pp. 229–242 (1982).)

The 435 bp NcoI fragment from the cDNA insert of δ1 was nick-translated and used to screen the above random-primed cDNA library to obtain δ4 and δ115. A 481 bp HindIII/SmaI fragment of the cDNA insert in δ115 was used to screen this library to obtain δ7a. Clones δ3b and δ7b were obtained using an oligonucleotide probe based on a sequence from δ115 (5'-TGGAACGTCGGAGAAAC-3').

Thus, additional clones were retrieved from this library, as follows: δ3b (829 bp), δ4 (1123 bp), δ7a (474 bp), δ7b (1378 bp), and δ115 (1362 bp). When these clones, and δ1 and δ2, were sequenced, overlapping portions of the genome, as illustrated in FIG. 1, were obtained. The sequencing data strongly suggested that the original HDV RNA was a circular molecule since the sequences of the 7 different cDNA clones could not be fitted into a linear molecule of only ~1700 nucleotides in length. This hypothesis was confirmed by visualizing circular HDV RNA molecules in the electron microscope under denaturing conditions. The complete sequence of DNA representing the genome and its complement is shown in FIG. 2, taking account of the overlapping portions of the various clones. The upper strand represents the HDV genomic RNA, the lower its complement. There was some sequence heterogeneity between the various clones, as indicated in FIG. 2, The heterogeneities in nucleotide sequence are indicated above the genomic strand. The effect on the amino acid encoded is indicated below the complementary strand; AM indicates an amber stop codon, and OP indicates an opal stop codon. Table 1 presents a comparison of the heterogeneities in several of the clones.

Table 2 shows putative polypeptides encoded by open reading frames (ORFs) of at least 300 nucleotides. The position of the first nucleotide in each open reading frame is indicated according to the numbering of the upper strands shown in FIG. 2, The upper strand, representing the genomic sequence is numbered 1–1679. Positions in the complement have the same numbers, but are preceded by x. Polypeptides encoded by regions of the complement thus are given with numbers in "reverse" order—e.g., x1619–x1014 for ORF5. The first nucleotide number in the table is that of the first nucleotide in the frame—not the ATG. The translational reading frame of ORF5 is shown in FIG. 2 (putative polypeptide p1 of Table 2) and a potential N-glycosylation site is indicated by *.

TABLE 1

Hepatitis δ cDNA Heterogeneity

| Heterogeneity (nucleotide no.) | Clone No. | | | | | | |
|---|---|---|---|---|---|---|---|
| | 115 | 7a | 1 | 7 | 2 | 7b | 3b |
| 118 | C | T | — | — | — | — | — |
| 264 | C | C | — | — | — | — | T |
| 390 | A | G | — | A | — | — | A |
| 414 | C | T | — | C | — | — | C |
| 488 | C | T | — | T | T | — | T |
| 553 | — | — | A | A | G | — | A |
| 589 | — | — | C | T | — | T | — |
| 603 | — | — | T | C | — | — | — |
| 653 | — | — | G | A | — | — | — |
| 987 | C | — | T | C | — | — | — |
| 1012 | T | — | C | T | — | — | — |
| 1024 | C | — | C | T | — | — | — |
| 1084 | T | — | — | A | — | T | — |
| 1141 | A | — | — | T | — | T | — |
| 1309 | T | — | — | C | — | — | — |
| 1413 | A | — | — | G | — | A | — |
| 1473 | T | — | — | — | — | C | — |
| 1567 | T | — | — | — | — | C | — |
| 1677 | A | — | — | — | — | G | — |

— = Not Determined or Not Within the Clone.

TABLE 2

| Strand | ORF number | Nucteotide #1 position | Total # of amino acids | Number of amino acids beginning with first methionine | Putative polypeptide |
|---|---|---|---|---|---|
| HDV RNA | 1 | 539 | 165 | 152 | p6 |
| HDV RNA | 2 | 786 | 156 | 121 | p7 |
| HDV RNA | 3 | 1609 | 121 | 0 | p9 |
| HDV RNA | 4 | 1297 | 115 | 68 | p9 |
| HDV RNA | 10 | 435 | 116 | 33 | p10 |
| HDV RNA | 11 | 937 | 119 | 96 | p11 |
| Anti-HDV RNA | 5 | 1619 | 221/202 | 214/195 Δ | p1 |
| Anti-HDV RNA | 6 | 1341 | 288 | 179/34 * | p2 |
| Anti-HDV RNA | 7 | 506 | 148/80 | 148/80 † | p3 |
| Anti-HDV RNA | 8 | 821 | 104 | 74 | p4 |
| Anti-HDV RNA | 9 | 91 | 101 | 0 | p5 |

* Ambiguity arising from clonal heterogeneity at position 1012 (FIG. 2).
† Ambiguity arising from clonal heterogeneity at position 264 (FIG. 2).
Δ Ambiguity arising from clonal heterogeneity at position 1012 (FIG. 2).

Nucleotide sequence analysis of clones containing the ORF5 region revealed several sequence heterogeneities in this region. These heterogeneities are indicated in FIG. 3, which shows the nucleotide sequence of ORF5. The heterogeneities in nucleotide sequence detected from other clones are listed above the nucleotide sequence. The amino acid substitutions resulting from the sequence heterogeneity is listed above the deduced amino acid sequence. As a result of this heterogeneity in sequence, ORF5 encodes a family of closely related polypeptides.

The heterogeneity at nucleotide position 608 of ORF5 (see FIG. 3) is of particular interest since, as discussed below, both viral polypeptides of $p24^\delta$ and $p27^\delta$ appear to encoded in ORF5. If position 608 contains an A, the resulting codon is an amber stop codon which would translate (unless the host contains an amber suppressor system) to yield a polypeptide the size of $p24^\delta$. However, if position 608 contains a G (of if the host has the ability to suppress the amber mutation), read through of the codon to the opal stop signal at position 664 yields a polypeptide the size of $p27^\delta$. This suggestion is supported by the finding that expression of ORF5 in E. coli D1210 transformed with porf5 yielded two products which are identifiable with the viral antigens $p24^\delta$ and $p27^\delta$ in terms of size and immunoreactivity (see §D.3). E. coli D1210 contains a leaky amber suppressor system; thus, a portion of translation terminates at the amber codon. Verification of the suggestion can be obtained by substituting G for A at position 608 of the ORF present in porf5. This substitution can be accomplished using in vitro site-directed mutagenesis, the techniques of which are known to those of average skill in the art.

The complete genome of HDV represents a 1679 nucleotide circular sequence. It is presumed that the genomic RNA is single-stranded, as only one of the complementary synthetic oligomers and single-stranded δ1 M13 probes hybridizes to the template. In addition, the template RNA cannot be translated in an in vitro rabbit reticulocyte lysate leading to the possibility that the genome is, in fact, representative of an anti-sense strand.

D.2. Confirmation of Polypeptide Encoding Clones

The viral RNA derived from infectious plasma was random primed, and the resulting cDNA was cloned into the PstI site of pBR322 using GC tailing as described above. The ligation mixtures were transformed into E. coli MC1061 and plasmid DNA prepared from a pool of about 20,000 recombinants. The plasmid DNA was cleaved with PstI and the cDNA inserts were eluted from an agarose gel, blunted with Klenow, ligated to EcoRI linkers, and then cloned into the phage vector λgt11 (Young, et al, Proc Natl Acad Sci USA (1983) 80:1194–1198) at the unique EcoRI site using Y1090 (r⁻) as host. This phage-random cDNA library was then screened using hybridization to two probes derived from the above-referenced δ4 and δ115 clones. In addition, colonies were immunoscreened using antisera derived from humans that were chronically coinfected with hepatitis B and δ viruses.

Several plaques were obtained which bound both the probes and also the antisera. One recovered plaque was sequenced and contained a cDNA of about 200 bp whose translational reading frame corresponded to part of polypeptide, p1 translated from the antigenomic strand shown in Table 2. The β-galactosidase fusion protein produced by this λgt11 thus contained at its carboxy terminus a region of polypeptide p1 that was responsible for the specific binding of δ antiserum. Control antisera from previous infections with hepatitis A, B, and non-A/non-B did not bind to this fusion protein. Accordingly, p1 evidently contains an antigenic region capable of specific binding to δ-infected antisera and thus is useful in diagnosis.

D.3. Construction of Expression Vectors and Expression of HDV Sequences

Figure 7:
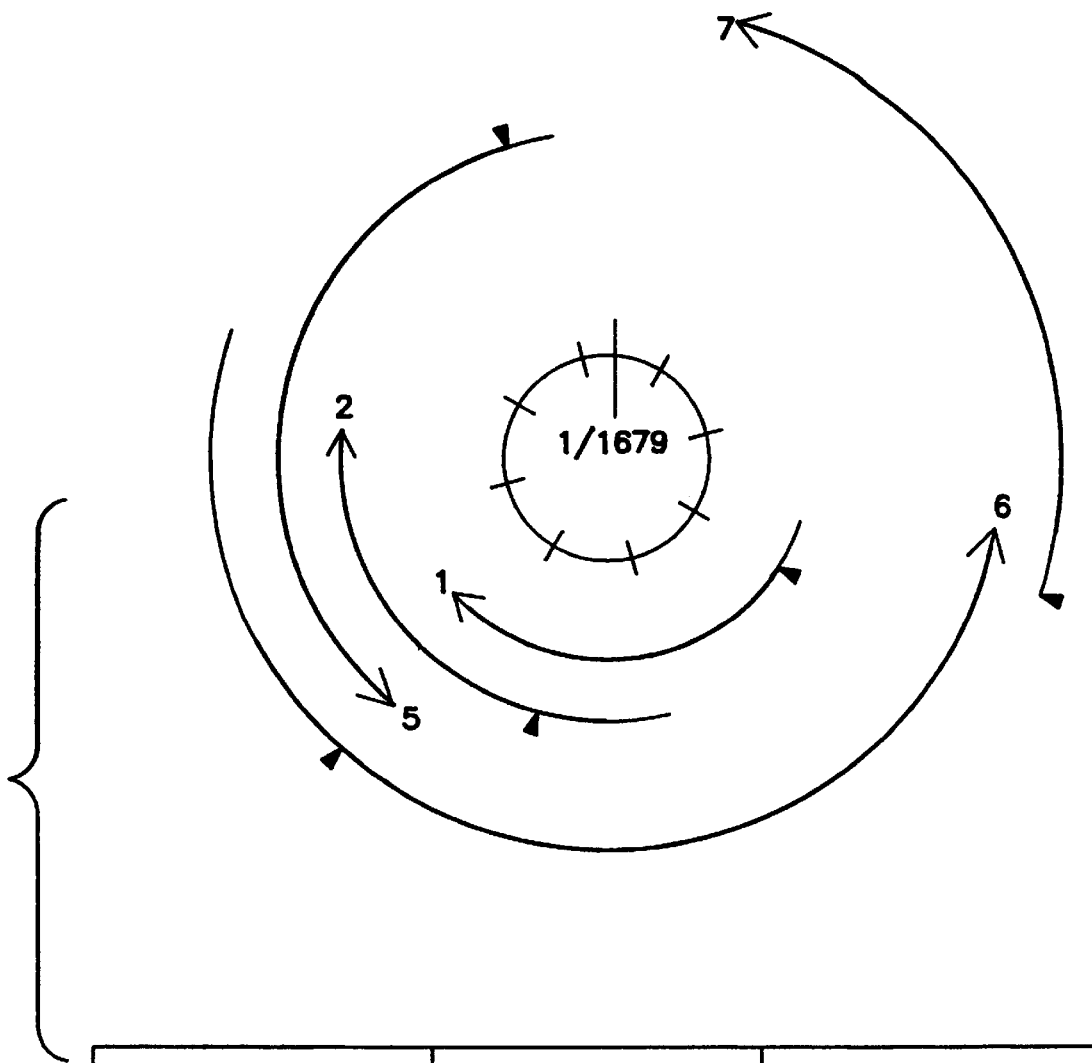
FIG. 7 shows the positions of the ORFs of the HDV genome and its complement.

The HDV genome and the complement contain a number of ORFs (see §D.1). Several of these ORFs have been expressed, and the antigenicity of the encoded polypeptides examined with respect to their ability to bind to HDV antiserum. FIG. 7 is a diagramatic representation of HDV ORFs. All HDV ORFs greater than 300 nucleotides beginning with an ATG are aligned with the circular coordinates of the HDV genome. The thick lines represent the portion of each ORF expressed in bacteria. The triangles ( ) denote the first in-frame ATG of each ORF. Arrows indicate translation of the genome or antigenomic strand, clockwise or counterclockwise, respectively. Coordinates of each entire ORF, the region expressed in bacteria and the relative translational frame are compiled in table form.

D.3.a. The Expression in E. coli of Fusion Proteins Containing HDV Polypeptide Encoded in ORF5 and ORF6

Bacterial expression plasmids were constructed which directed the synthesis of fusion proteins containing human superoxide dismutase (SOD) (Hallewell. et al, Nucleic Acids

*Res* (1985) 13:2017) and also portions of HDV protein encoded within ORF5 or ORF6, i.e., p1 and p2, respectively. The plasmids synthesized most of the ORF5-encoded p1 or ORF6-encoded p2 fused to the carboxy terminus of SOD.

The expression plasmids were based on the tac promoter driven expression plasmid pSOD16 of Hallewell et al (supra). Plasmid pSOD16cf2 was generated from pSOD16 by replacement of a portion of the carboxy terminal coding region of the SOD gene and downstream polylinker sequences through the MboI site by the new polylinker sequence.

```
5' GATCGCCATGGGTACCCGGGTCGACTAAATGACTAG 3'

3' CGGTACCCATGGGCCCAGCTGATTTACTGATCTTAA 5'
```

The substitution of this polylinker sequence results in the removal of the natural carboxy terminal Gln of SOD.

To insert the sequence derived from the HDV genome, the method of Steimer et al, *J Virol* (1986) 58:9–16, was followed. pSOD16cf2 was suitably digested in order to accommodate the particular coding sequence desired as described below.

For p1, the recovered DNA clone, δ115, was digested with SstII, blunted with Klenow, and then digested with SalI to recover a 600 bp fragment isolated from an agarose gel. The isolated fragment was ligated into pSOD16cf2 which had been digested with NcoI, blunted, and then digested with SalI to yield pSOD-δp1. The fusion protein encoded containing 205 residues of the p1 amino acid sequence encoded by nucleotides x1567 to x963.

For the p2 protein, the recombinant DNA plasmid δ4 was digested with EcoRI and SmaI to recover a 622 bp fragment which was ligated into EcoRI/SmaI-digested pSOD16cf2 to yield pSOD-δp2.

(Both of the resulting plasmids were sequenced to confirm the location and orientation of the p1 and p2 encoding sequences at the C-terminus of the SOD protein.)

The ligation products were transformed into *E. coli* D1210 (Sadler et al, *Gene* (1980) 8:279–300). Single colony transformants were grown overnight at 37° C. in 2 ml L-broth plus 100 μg/ml ampicillin. Glycerol (50%) stocks of these cultures were prepared and stored at −20° C.

For protein expression analysis, overnight cultures, in medium as above, were begun from glycerol stocks. These cultures were diluted 1/100 into the same medium and grown at 37° C. to an $OD_{650}$ of 0.6 when aliquots were either lysed or induced for maximum expression by the addition of 1 mM IPTG and further incubation for 4 hours prior to lysis.

Cells were lysed in the presence of SDS and DTT for analysis on denaturing polyacrylamide gels (Laemmli. *Nature* (1970) 277:680) and were immunoblotted according to Towbin et al, *Proc Natl Acad Sci* USA (1979) 76:4350. The results are shown in FIG. 6.

Immunoblots were reacted with δ antiserum from chronically infected patients (panel A) or control antisera (panel B) containing antisera infected with non-δ hepatitis viruses. In addition, after prebinding with 5% goat serum, the immunoblots were reacted with a 1:300 dilution of antisera diluted in 1× PBS containing 0.3% Tween-20 and 5% goat serum, followed by incubation with 1:200 dilution of horseradish peroxidase-conjugated goat antihuman IgG and the blot was developed in the presence of the chromogen 4-chloro-1-naphthol (Biorad).

In FIG. 6 lanes 1–4 contained extracts of cells containing the pSOD-δp1 recombinant vector; lanes 5 and 6 contained extracts from cells transformed with the host vector; lanes 7–10 contained the corresponding pSOD-δp2 recombinant vectors. The samples of lanes 3, 4, 6, 9, and 10 were from cultures uninduced with IPTG; those from the remaining lanes, 1, 2, 5, 7, and 8 were from cultures further induced with IPTG. The presence of additional protein bands in lanes 1–4 as compared to lanes 5–10 shows the production of an antigenically reactive protein from pSOD-δp1, designated SOD-δp1, but not from pSOD-δp2. Thus, ORF5 but not ORF6 encodes protein which specifically bind human HDV antiserum. The failure to detect–specific immunoreactive ORF6 fusion polypeptides was not due to a lack of expression in the bacterial host since, when monitored for binding to rabbit antiserum raised against human superoxide dismutase, the products expressed from pSOD-δp1 and pSOD-δp2 were present at similar levels.

As seen in FIG. 6*a*, there are predominantly two translation products from pSOD-δp1 which are immunoreactive with HDV antiserum. The estimated size of the largest major immunoreactive ORF5 polypeptide is 49,000 daltons, which is consistent with a fusion polypeptide containing 154 amino acids of superoxide dismutase and 205 amino acids specified by ORF5. This polypeptide may result from suppression of the amber codon in ORF5 (see FIG. 2). The amber codon is present in pSOD-δp1, and the host strain, *E. coli* D1210, is an amber suppressor strain. The second major polypeptide product, which is smaller, may have resulted from leakiness in the suppression, thus allowing termination at the amber codon. Other possible alternative explanations are that the smaller protein(s) may result from postranslational processing of a single product, or that there are alternate initiation sites within the ORF5 coding region.

A sample of *E. coli* strain D1210 (pSOD-δp1) has been deposited with the American Type Culture Collection (ATCC), 12310 Parklawn drive, Rockville, Md. 20852, and has been assigned Accession No. 67131. This deposit will be maintained under the conditions specified in the Budapest Treaty.

D.3.b. The Expression in *E. coli* of Fusion Proteins Containing HDV Polypeptide Encoded in ORFs 1, 2, and 7

Bacterial expression vectors which directed the synthesis of fusion proteins containing portions of SOD and of HDV proteins encoded within ORFs 1, 2, and 7, i.e., the vectors pSOD-orf1, pSOD-orf2, and pSOD-orf7, were constructed. The construction conditions, and sequencing, were as described for pSOD-δp1 and pSOD-δp2 in §D.3.a., except for the following.

For pSOD-orf1, the 436 b.p. insert fragment was isolated from clone δ1 by digestion of the plasmid with NcoI, followed by gel purification. This fragment was ligated to NcoI treated, phosphatased, pSOD16cf2. The ORF1 fragment in the clone has the genomic orientation.

For pSOD-orf2, the 593 b.p. insert gel purified fragment was isolated after digestion of clone δ115 with BstXI, followed by treatment with Klenow, and then digestion with EcoRI. This fragment was ligated to pSOD16cf2 which had been digested with NcoI, blunt ended with Klenow, and digested with EcoRI.

For pSOD-orf7, a 439 bp insert gel purified fragment was isolated after digestion of clone δ115 with AluI and SmaI. This fragment was ligated to pSOD 16cf2 which had been SmaI digested and phosphatased, Proteins expressed in pSOD-orf1, pSOD-orf2, and pSOD-orf7 were analyzed by immunoblot as described for pSOD-δp1 and pSOD-δp2 (see §D.3.a.).

The expression conditions were also as described in §D.3.a. The presence of ORF1, 2 and 7 hSOD fusion products in the bacterial lysates was demonstrated by partial reactivity with rabbit anti-hSOD polyclonal antibodies against hSOD. Lysates of bacterial cultures expressing each of the ORFs were immunoblotted onto nitrocellulose and incubated with individual antisera from 12 different patients with chronic HDV infections. The products expressed from pSOD-orf1, pSOD-orf2, and pSOD-orf7 did not bind to HDV antisera, although a product expressed from pORF5, the construction of which is described in §D.3.c., did bind the HDV antisera.

D.3.c. The Expression in *E. coli* of Unfused HDV Polypeptides Encoded in ORF5

A bacterial expression plasmid was constructed which directed the synthesis of unfused ORF5 encoded polypeptides. This vector, porf5, was similar to that used to express fused sod-orf polypeptides (pSOD-δp1, see §D.3.a.), except that it contained a second synthetic linker designed to terminate translation after the hSOD coding sequence and to reinitiate translation at the first ATG of the HDV sequence. This linker encodes 10 amino acids originally present in ORF5, including the amino terminal ATG. More specifically, the vector was constructed by ligating together the following: a) a 605 b.p. SstII/SalI fragment which was restricted from δ115 and gel purified; b) the second linker: and c) the large vector fragment obtained by treating pSOD16cf2 with NcoI and SalI. The linker sequence was:

```
5' CATG GCT ACA GAG GAA TTA TAAT ATG AGC CGG TCC

3' CGA TGT CTC CTT AAT ATTA TAC TCG GCC AGG

GAG TCG AGG AAG AAC CGC 3'

CTC AGC TCC TTC TTG G 5'
```

Transformation of *E. coli* D1210 with the plasmid porf5 was as described in § D.3.a for transformation with other plasmids. The construction of the insert in porf5 was confirmed by DNA sequence analysis. This analysis also confirmed the presence of the amber codon in the δ115 derivative of ORF5 (see FIG. 3 for the ORF5 sequence heterogeneities).

Figure 8:
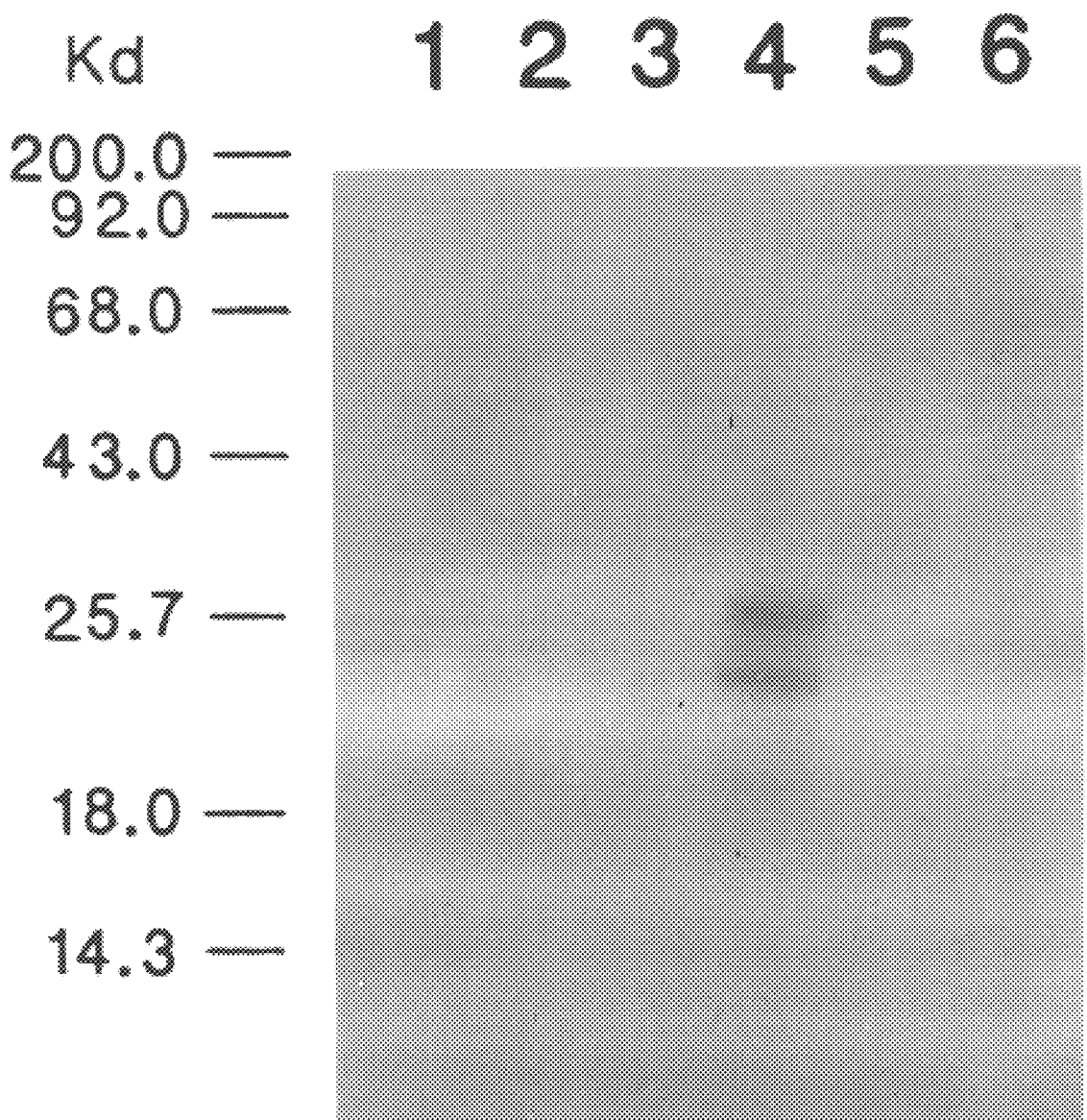
FIG. 8 shows an immunoblot using HDV antiserum of the expressed products of ORFs 1, 2, 6, and 7 fused to SOD, and of the unfused expression product of ORF5.

Expression of ORF5 polypeptides encoded within porf5, and immunoreactivity of the expressed products with HDV antisera was carried out as described in § D.3.a., and was simultaneous with the analysis of the expressed products from pSOD-orf1, pSOD-orf2, and pSOD-orf6, and pSOD-orf7. As seen in FIG. 8, which shows an immunoblot, only the ORF5 encoded polypeptides bound to HDV antisera, and these polypeptides did not bind to antisera from uninfected individuals.

For the immunoblot analysis in FIG. 8, bacterial cultures harboring control plasmid (pSOD16cf2) or hSOD-orf1, 2, 6, 7 and ORF5 expression plasmids were induced with IPTG for approximately four hours. Cells were pelleted, lipid and protein from 0.024 D equivalent of cells were electrophoresed on 12% Laemmli gels as described in § D.3. Protein was transferred onto nitrocellulose filters in carbonate buffer. Immunoblots were incubated with a 1:200 dilution of human HDV antiserum followed by incubation with $^{125}$I-labeled sheep antihuman IgG antibody, and washed as described in §D.3.a. Lysates appear in the following order: lane 1, pSOD16cf2; lane 2, pSOD-orf1; lane 3, pSOD-orf2; lane 4, porf5; lane 5, pSOD-orf6; and lane 6, pSOD-orf7.

FIG. 8 also shows that the products expressed from porf5 which react with HDV specific antibodies are of two molecular weight species, approximately 27 k and 24 k. As described below, these polypeptides contain immunogenic epitopes shared by both hepatitis viral polypeptides p27$^δ$ and p24$^δ$. The presence of 27 kd and 24 kd polypeptides in HDV has been recently reported. Bergmann, K. F., and Gerin, J. L., *J of Inf Diseases* (1986) 154:702; and Bonino, F., et al, *J Virol* (1986) 58:945. In addition, as shown below, these polypeptides also probably comprise the hepatitis delta antigen (HDAg). HDAg was originally found in the nuclei of hepatocytes of infected individuals. Rizzetto, M., et al, *Gut* (1977) 18: 997.

D.3.d. The Expression in Yeast of HDV Polyeptides Encoded in ORF5, and Partial Purification of the Product A yeast expression vector was constructed which directed the synthesis of required ORF5 encoded HDV polypeptides. Expression of this plasmid, pYAG-δp1, in yeast strain AB 110 yielded a 195 amino acid polypeptide which is immunologically reactive with HDV antiserum, and which is putatively viral protein p24$^δ$.

The yeast expression vector, pYAG-δp1, was constructed as follows: First, pAG-δp1 was constructed by inserting ORF5 from clone δ115 ligated to a new linker, into an expression cassette in PBS100. The cassette, which can be expressed with BamHI contains an ADH2-GAP regulatable promoter upstream of the unique NcoI site and a GAP terminator downstream of a unique SalI site. After cloning pAG-δp1 in *E. coli* HB101, the ORF5 containing expression cassette was restricted from pAG-δp1 with BamHI, and ligated into the yeast shuttle. vector pAB24, which had been restricted with BamHI. The resulting plasmids were cloned in *E. coli* HB101, and a shuttle plasmid, pYAG-δp1, was selected; for expression of ORF5, yeast strain AB110 was transformed with this plasmid to yield AB110(pYAG-δp1).

A sample of yeast strain AB110(pYAG-δp1) has been deposited with the ATCC, 12301 Parklawn Drive. Rockville, Md. 20852, and has been assigned Accession No. 20845. This deposit will be maintained under the conditions specified in the Budapest Treaty.

More specifically, the ORF5 containing expression cassette was constructed by ligating the following: a gel-purified 605 b.p. fragment obtained by digesting clone δ115 with SstII and SalI; a new linker (linker 3); and a gel-purified 5841 b.p. fragment obtained by digesting PBS100 with NcoI and SalI. The sequence of linker 3 was:

```
5' CATG AGC CGG TCC GAG TCG AGG AAG AAC CGC 3'

TGC GCC AGG CTC AGC TCC TTC TTG G
```

The plasmid PBS100 is described in U.S. Pat. application Ser. No. 760,197, which is assigned to the herein assignee, and which is hereby incorporated by reference. This plasmid contains a yeast expression cassette cloned into pAB12, a pBR322 derivative. The expression cassette contains a hybrid ADH2-GAP promoter, a GAP terminator, and non-essential sequences between the NcoI and SalI sites; these latter sequences were replaced with the ORF5 region from clone δ115. The ADH2-GAP promoter is a 1200 bp BamHI-NcoI fragment isolated from plasmid pJS103.

Plasmid pJS103 was constructed as follows: The ADH2 portion of the promoter was constructed by cutting a plasmid containing the wild-type ADH2 gene from plasmid pADR2 (Beier et al, *Nature* (1982) 300:724–728) with restriction enzyme EcoRV, which cuts at position +66 relative to the ATG start codon, as well as in two other sites in pADR2, outside of the ADH2 region. The resulting mixture of a vector fragment and two smaller fragments was resected with Ba 31 exonuclease to remove about 300 bp. Synthetic XhoI linkers were ligated onto the Ba 31-treated DNA. The resulting DNA linker vector fragment (about 5 kb) was separated from the linkers by column chromatography, cut with restriction enzyme XhoI, religated, and used to transform E. coli to ampicillin resistance. The positions of the XhoI linker were determined by DNA sequencing. One plasmid which contained an XhoI linker within the 5' nontranscribed region of the ADH2 gene (position −232 from ATG) was cut with the restriction enzyme XhoI, treated with nuclease S1, and subsequently treated with the restriction enzyme EcoRI to create a linear vector molecule having one blunt end at the site of the XhoI linker and an EcoRI end. The GAP portion of the promoter was constructed by cutting plasmid pPGAP1 with the enzymes BamHI and EcoRI, followed by the isolation of the 0.4 Kbp DNA fragment. This purified fragment was then completely digested with the enzyme AluI and an approximately 200 bp fragment was isolated. This GAP promoter fragment was ligated to the ADH2 fragment present on the linear vector described above to give plasmid pJS103.

The plasmid pPGAP1 is a yeast expression cassette vector which has a polyrestriction site linker between the GAPDH terminator and a truncated GAPDH promoter region. The polyrestriction site contains the recognition sites for NcoI, EcoRI, and SalI, and the cassette is excisable as a BamHI fragment. The preparation of pPGAP1 is described in EPO O 164 556 and Travis, J., et al, J Biol Chem (1985) 260(7):4384–4389. In both references pPGAP1 is referred to PPGAP.

Plasmid pAB12 is a pBR322 derivative which lacks the region between the unique HindIII and SalI sites, and contains a BamHI linker in the unique EcoRI site. The vector was constructed by digesting pBR322 to completion with HindIII and SalI, followed by limited digestion with Bal 31 nuclease. The resulting ends were eluated with Klenow and the blunted ends ligated with T4DNA ligase to reform closed covalent circles. These circles were then digested to completion with EcoRI, the overhangs filled in with Klenow, and the blunt ends were ligated with BamHI linkers. Excess linkers were removed by digestion with BamHI, and covalently closed circles were formed by ligation.

Figure 9:
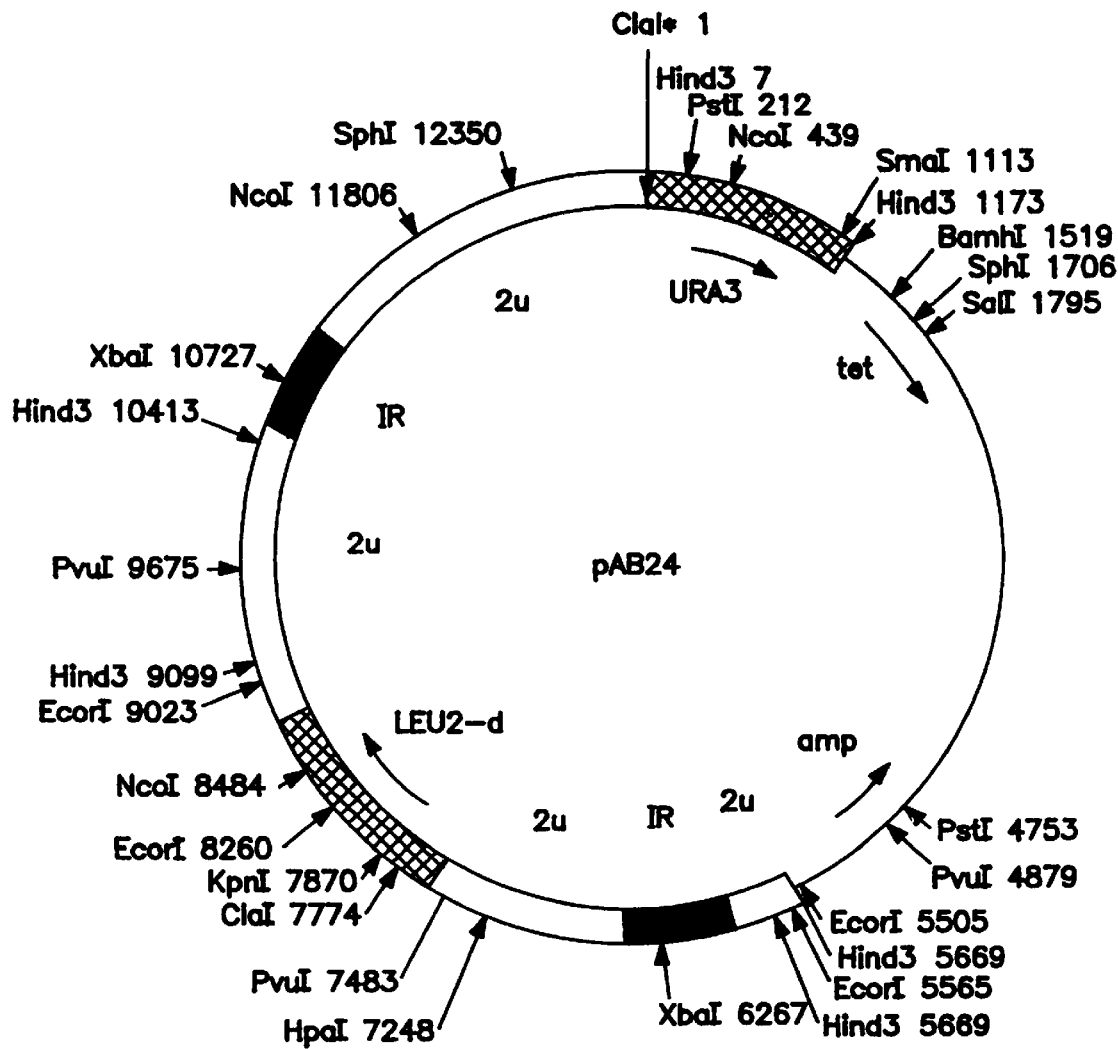
FIG. 9 is a restriction map of pAB24, including some genetic features.

Plasmid pAB24 is a yeast shuttle vector which contains the complete 2μ sequence (Broach, in Molecular Biology of the Yeast Saccharomyces, 1:445, Cold Spring Harbor Press (1981)) and pBR322 sequences. It also contains the yeast URA3 gene derived from plasmid YEp24 (Botstein, et al, (1979) Gene 8:17) and the yeast $LEU^2d$ gene derived from plasmid pC1/1 (described in European Patent Application publication No. EPO O 116 201). Plasmid pAB24 was constructed by digesting YEp24 with EcoRI and religating the vector to remove the partial 2μ sequences. The resulting plasmid. YEp24ΔRI. was linearized by digestion with ClaI and ligated with the complete 2μ plasmid which had been linearized with ClaI. The resulting plasmid, pCBou, was then digested with XbaI and the 8605 bp vector fragment was gel isolated. This isolated XbaI fragment was ligated with a 4460 bp XbaI fragment containing the $LEU^2d$ gene isolated from pC1/1; the orientation of the $LEU^2d$ gene is in the same direction as the URA3 gene. Insertion of the expression cassette was in the unique BamHI site of the pBR322 sequences, thus interrupting the gene for bacterial resistance to tetracycline. FIG. 9 presents a map of pAB24, showing the restriction enzyme sites and some distinctive features.

Expression of ORF5 in yeast was accomplished using yeast strain AB110 which had been transformed with pYAG-δp1. Yeast strain AB110 has been described in U.S. patent application Ser. No. 620,662, which is assigned to the herein assignee, and which is hereby incorporated by reference. The genotype of AB110 is MATα, ura 3-52, leu2-04 or both leu 2-3 and leu 2-112, pep 4-3, his 4-500 [cir°].

For expression, cells from a frozen stock were streaked onto Leu⁻ plates and incubated at 30° C. A single colony was inoculated into Leucine selective media [synthetic minimal media, amino acid supplement (w/o Leu). 8% glucose; Sherman et al in Laboratory Manual for Methods in Yeast Genetics; Cold Spring Harbor Laboratory 1986. pp. 163–169; and the culture was incubated with shaking at 30° C. 2 ml of the culture were then inoculated into 100 mls Leu⁻ Media, 3% glucose and incubated with shaking at 30° C. When the culture had reached saturation. 50 mls was inoculated into 1l of Leu⁻ media, 1% glucose. The culture was incubated with shaking at 30° C. until the density was measured at $OD_{650}$=1.75 OD/ml at which point the cells were pelleted and either stored at −80° C. or processed for protein purification.

Orf 5 encoded proteins expressed in yeast were partially purified as follows. The yeast expression culture. AB10 (pYAG-δp1). was pelleted and the volume of packed cells was estimated. The δp1 protein was purified using the glass bead lysis method. The cell pellet was resuspended in 2 volumes (vol.) of Buffer I (50 mM Tris-HCl pH 8.0, 1 mM EDTA, 1 mM phenylmethyl sulfonyl fluoride (PMSF). 1 ug/ml pep5tatin A) and 1 vol. of glass beads (0.25 mm, acid and heat treated). The cells were lysed by vigorous vortexing and kept at 4° C. The suspension was centrifuged, the supernatant was removed, and the cell pellet was washed in 2 vol. Buffer I, 1% Triton X-100 and then centrifuged. The supernatant was removed and the pellet was washed 3 times with 2 vol. of Buffer I; during the last wash the glass beads were removed from the protein suspension. The washed pellet was extracted 2 times with equal volumes of Buffer I, 6M Urea to solubilize the protein. The supernatants were combined and diluted 1:10 with Buffer I and stored at 4° C. with 20 mM sodium azide as a preservative. The final step before use of the protein was to dialyze twice in 100–300 vol, of Buffer I without PMSF and pepstatin.

D.4. Identification of Polypeptides Encoded Within ORF5

The polypeptides encoded within ORF5 were identified as those of $p27^δ$ and $p24^δ$, by direct comparison of the sizes expressed in bacteria recombinant unfused polypeptides with that of the $p27^δ$ and $p24^δ$ present in HDV particles and in HDAg-positive liver extracts. The ORF5 encoded polypeptides were further identified as $p27^δ$ and $p24^δ$ on the basis of immunological competition between the recombinant polypeptides expressed in yeast and $p27^δ$ and $p24^δ$ for HDV antibodies. Finally, the ORF5-encoded polypeptides were identified as components of nuclear HDAg by the competitive binding of the recombinant polypeptides with the nuclear HDAg, as monitored by indirect immunoperoxidase staining of HDV-infected liver slices.

D.4.a. Comparison of Anti-HDV Antibody Binding Polypeptides Expressed in Bacteria from porf5 with $p24^δ$ and P27δ in HDV Particles and in HDV Infected Liver The expression of the ORF5-encoded polypeptides from ports in bacteria, and the preparation of the lysates were as described above in §D.3. Lysates of HDV particles and of HDV infected liver were kindly prepared by K. F. Bergmann according to the procedure described by K. F. Bergmann and J. L. Geria. *J of Inf Diseases* (1986) 154:702, which is hereby incorporated by reference. In the preparation of liver lysates, liver samples were minced with scissors and washed with PBS followed by homogenization with a Potter-Elvejem Apparatus in 6M guanidinium HCl (pH 6). After 1–3 hr of incubation at 4° C. the extracts were centrifuged at 1500 g for 10 min. dialyzed against PBS, and centrifuged again. Viral lysates were prepared by modifying the reported procedure to omit the BSA. Serum samples were layered over 20% sucrose, 0.02M HEPES (pH 7.4), 0.01M CaCl2, 0.01M Mg Clr, and were centrifuged in an SW 41 rotor for 5 hr at 150,000 g to pellet the virus. The pellets were held in 0.05M Tris (pH 6.8) and 2% SDS.

Figure 10A:
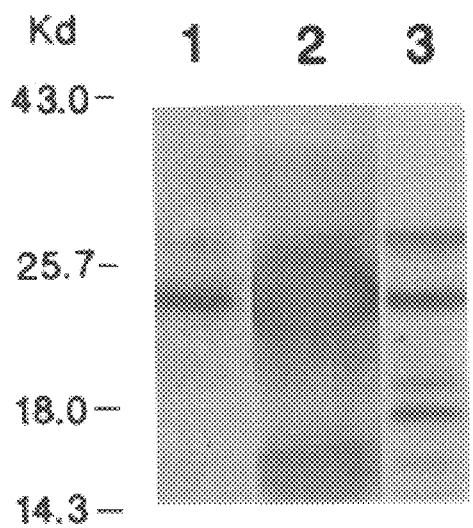
FIG. 10A shows an immunoblot using HDV antiserum of the unfused ORF5 produce expressed in *E. coli* compared to antigens present in HDV particles and in infected liver lysates.
Figure 10B:
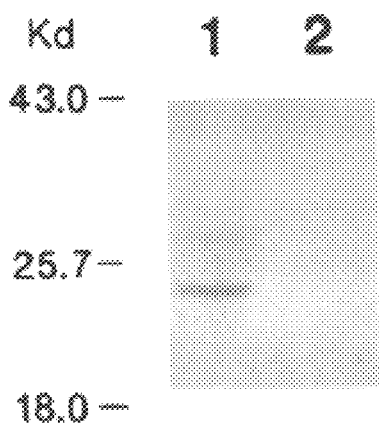
FIG. 10B shows an immunoblot demonstrating the competition for HDV antibodies between ORF5 product expressed in yeast with $p24^\delta$ and $p27^\delta$ present in HDV particles.
Figure 10C:
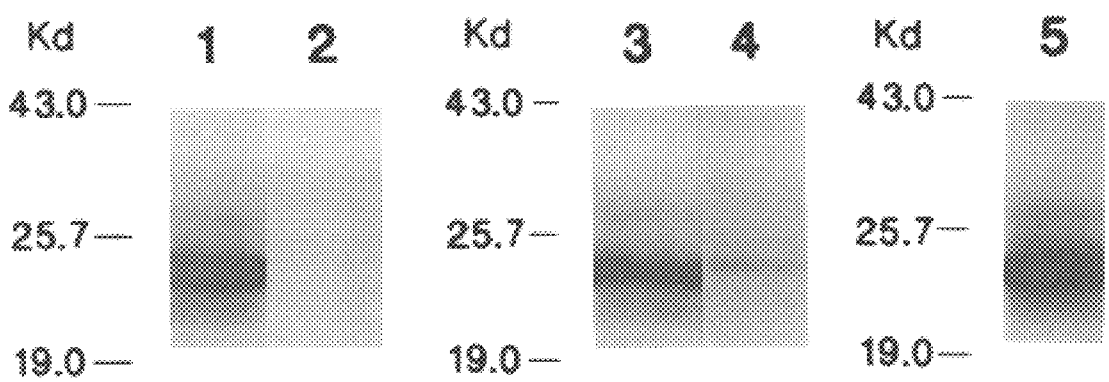
FIG. 10C shows an immunoblot demonstrating the competition for HDV antibodies between ORF5 product expressed in yeast and bacteria with $p24^\delta$ and $p27^\delta$ present in HDV infected liver.

Lysates of bacteria expressing ORF5 were electrophoresed in lanes adjacent to extracts of pelleted HDV or extracts of HDAg positive liver on 12% Laemmli gels, immunoblotted on nitrocellulose and incubated with HDV antiserum (1:400 dilution). FIG. 10A shows the immunoblot of extracts of HDV virus (lane 1), of infected liver lysate (lane 2), and a lysate of bacteria after expression of porf5 (lane 3). As seen in FIG. 10A, two major immunoreactive polypeptides in the bacterial lysates appeared to comigrate with the p27$^\delta$ and p24$^\delta$ polypeptides extracted from pelleted virus and from HDAg-positive liver. Several low molecular weight immunoreactive polypeptides were also present in the bacterial lysate; these may represent proteolytic products of p27 and/or p24.

D.4.b. Immunological Competition Between ORF5 Polypeptide Expressed in Yeast or Bacteria and P24$^\delta$ and P27$\delta$ in HDV Particles or in HDV Infected Liver Immunological competition between recombinant ORF5 products and viral peptides, p24$^\delta$ and p27$^\delta$ was determined by competitive binding assays. In general the HDV antiserum was allowed to absorb to the recombinant ORF5 products produced either in yeast or in bacteria. The preabsorbed serum was compared to control serum as to its ability to bind to viral $p24^{\delta}$ and $p27^{\delta}$ in an immunoblotting procedure. The control serum was HDV antiserum which had been preabsorbed with the expression products of yeast or bacterial cultures transformed with the control (parental) vectors. The expression conditions were those which allowed expression of the recombinant vectors containing ORF5.

Immunological competition between ORF5 products expressed in yeast strain AB110 transformed with pYAG-$^{\delta}$p1 and $p24^{\delta}$ and $p27^{\delta}$ in HDV particles was determined as follows. The recombinant ORF5 products were expressed in yeast and partially purified under the conditions described in §D.3. Extracts of HDV particles were prepared, read on Laemmli gels, and blotted as described in §D.4.a., except that in the immunoblotting procedure 5% nonfat milk in 1× PBS (0.14M NaC1. 2.5 mM K C1, 1.5 MM K $H_2PO_4$, 8 mM $Na_2H$ $PO_4$. 12 H2O, pH=7.4) was used as a blocking agent prior to incubation of nitrocellulose filters with HDV antiserum. The blotted HDV polypeptides were incubated with HDV antiserum which had been preabsorbed with extracts from 0.44 ml of yeast culture (OD 650, 16 OD/ml) expressing either: (1) the parental control plasmid, pAB 24; or (2) the ORF5 containing plasmid. pYAG-δp1.

FIG. 10B presents the immunoblots using HDV antiserum preabsorbed with-lysates of yeast expressing either the control plasmid (lane 1); or the ORF5 containing plasmid (lane 2). As seen in the figure, preabsorption of the HDV antiserum with the recombinant ORF5 polypeptides completely eliminated antibody binding to HDV polypeptides $p24^{\delta}$ and $p27^{\delta}$; preabsorption with ADV antiserum preabsorbed to the control lysate did not prevent the binding. The weak, diffuse band in FIG. 10B. lane 2, may represent nonspecific binding, since it was also present when control sera lacking HDV antibodies replaced HDV antiserum. From the binding in common of the polyclonal antibodies in the HDV antiserum, it may be deduced that the ORF polypeptides were immunologically identifiable as $p24^{\delta}$ and $p27^{\delta}$.

Immunological competition between ORF5 polypeptides expressed in bacteria or yeast and $p24^{\delta}$ and $p27^{\delta}$ in infected liver was also determined. The expression of ORF5 polypeptides in yeast strain HB110 (pYAG-δp1) was as described immediately above: expression of ORFs polypeptides in *E. coli* D1210 transformed with porf5 was under the conditions described in § D.3. Liver lysates were prepared and blotted as described in § D.4.a., except that the above described modification in the blotting procedure was also used. The blots of the polypeptides in HDAg positive liver extracts were incubated with HDV antiserum which had been pre-incubated with the following: extracts of yeast cultures AB110 expressing pAB24 (control); extracts of yeast cultures AB110 expressing ORF5 from pYAG-δp1; extracts of *E. coli* D1210 expressing pSOD16cf2 (control); and extracts of *E. coli* expressing porf5. Preabsorption of the HDV antiserum with: (1) the yeast cultures was with 0.44 ml of $OD_{650}$, 16 OD/ml; and (2) *E. coli* was with approximately 100 ml of O.D.$_{650}$ 0.6 OD/μl. The blots were incubated with 1:1000 dilutions of the preabsorbed HDV antiserum. In addition, as a control, a blot was incubated with HDV antiserum which was preincubated with an equal volume of dialyzed urea extraction buffer.

FIG. 10C presents the immunoblots of HDV polypeptides using the serum preabsorbed with: yeast expressing the control plasmid (lane 1); yeast expressing ORF5 (lane 2); *E. coli* expressing the control plasmid (lane 3); *E. coli* expressing ORF5 (lane 4); and buffer control (lane 5). As seen in the figure, preabsorption of HDV antiserum with ORF5 polypeptides expressed in yeast completely eliminated the binding of HDV specific antibodies to $p27^{\delta}$ and $p24^{\delta}$ in HDAg-positive liver extracts. Orf 5 polypeptides from bacterial cultures also appeared to eliminate the binding of HDV specific antibodies to $p27^{\delta}$, and reduced the binding of these antibodies to $p24^{\delta}$ by at least 10 fold based on densitometry tracings of the original autoradiograms. The residual binding of HDV antiserum to $p24^{\delta}$ is probably due to the limiting amount of the ORF5 polypeptide in bacterial extracts. In none of the controls was there a significant reduction in the binding of HDV antigen to $p24^{\delta}$ and $p27^{\delta}$ from HDAg infected liver.

D.4.c. Immunological Competition Between ORF 5 Encoded Polypeptides and Nuclear HDAg in HDV Infected Liver Section of HDAg positive liver were incubated with HDV antiserum which had been preabsorbed with ORF5 encoded polypeptides expressed in yeast, or with a control lysate. The preparation of the preabsorbed HDV antiserum including controls, was as described in §D.3.B. The sections were subsequently incubated with a peroxidase labeled antihuman IgG, and indirect immunoperoxidase staining was performed. The procedures were according to Govindarajan, S., et al, *Histopathology* (1984) 8:63, which is hereby incorporated by reference. In this method, a preliminary blocking of endogenous peroxidase was carried out. Deplasticized sections were incubated with preabsorbed HDV antiserum for 30 min, in a moist chamber at RT, followed by 2 washes with PBS and treatment with horseradish peroxidase conjugated rabbit antihuman IgG in a moist chamber. Subsequently, the sections were rinsed in PBS for 10 min, and treated for 5–8 min, with 3–3' diamino-benzidine hydrochloride and hydrogen peroxide. After dehydration the sections were cover slipped and examined by light microscopy.

Figure 11A:
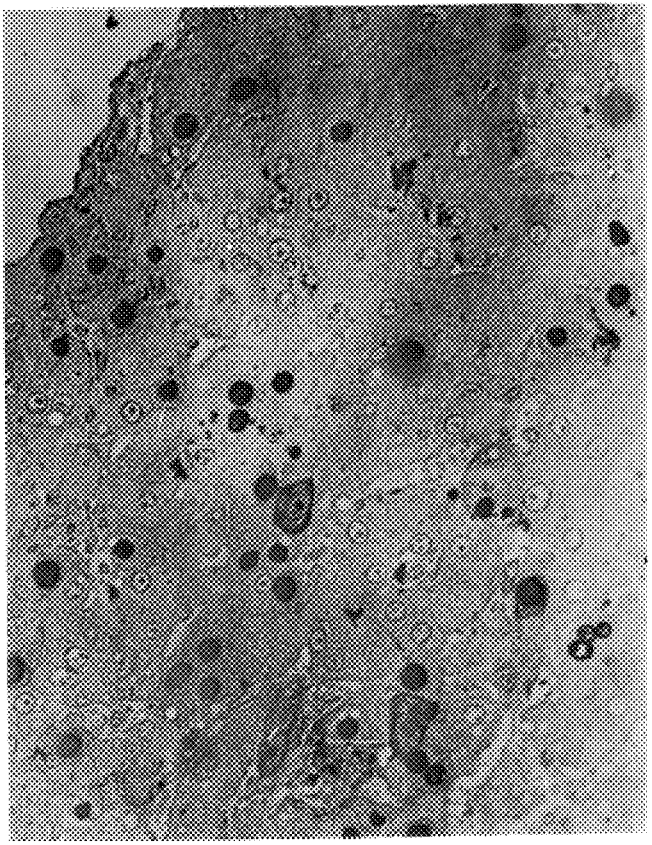
FIG. 11 shows liver slices stained by an indirect immunoperoxidase staining method demonstrating that ORF5 product expressed in yeast competes with liver HDV δ antigen for HDV antibodies.
Figure 11B:
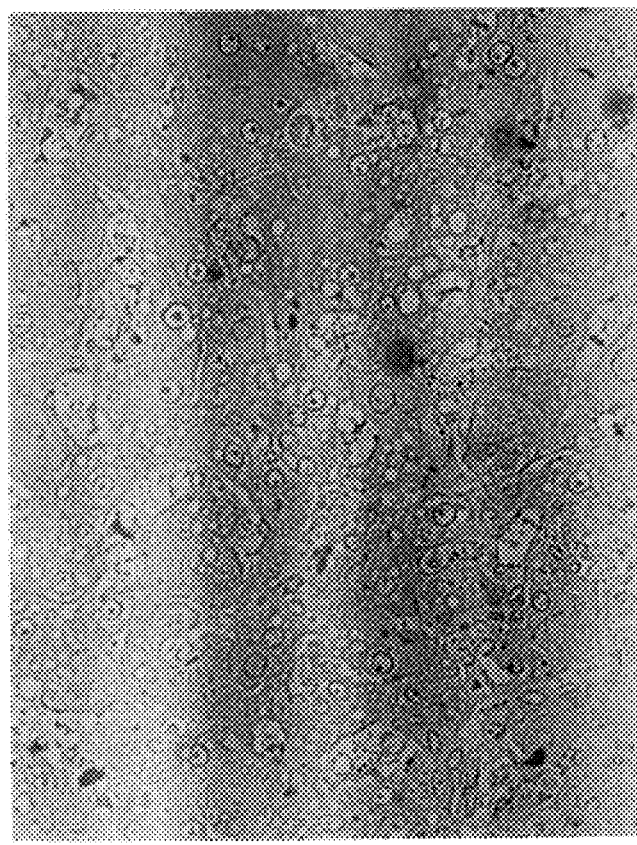

FIG. 11 shows photographs of the stained liver sections. The photographs were taken at a magnification of 150×. FIG. 11A shows the indirect immunoperoxidase staining obtained with HDV antiserum incubated with the control yeast lysate. FIG. 11B shows the staining when the HDV antiserum is preabsorbed with ORF5 encoded polypeptides expressed in yeast. In contrast to the clear binding to nuclei of antibodies against HDAg observed in HDV antiserum preabsorbed with the control extract, there was no binding when the antiserum was preabsorbed with the recombinant ORF5 polypeptides.

Heretofore direct evidence that $p24^\delta$ and $p27^\delta$ are components of nuclear delta antigen has been lacking. The data provided above indicates that the ORF5 encoded products compete with the nuclear delta antigen for HDV specific antibodies. The data also show that ORF5 encodes 2 polypeptides which are the same size as $p24^\delta$ and $p27^\delta$, and which have the same immunoreactive epitopes as those viral polypeptides. Hence, the combined data show that ORF5 encodes viral polypeptides $p24^\delta$ and $p27^\delta$, and that these polypeptides are components of nuclear delta antigen in HDV infected liver.

D.5. Hybrid Particle HDV Immunogens

U.S. Ser. No. 650,323, filed Apr. 12, 1984 and assigned to the same assignee is incorporated herein by reference. This application describes the construction of hybrid particles of hepatitis B surface antigen (HBsAg) containing inserts of foreign immunogens into a presurface (pre-S) coding portion in reading frame with the codons for HBsAg. Plasmid pDC101, described therein contains a portion of the pre-S/HBsAg gene, including 55 codons of the pre-S region, in a GAPDH controlled expression cassette cloned into the BamHI site of a pBR322 derivative. The incorporated application describes the insertion of desired immunogens, such as the gD (glycoprotein D) antigenic site into a unique EcoRI site present in the pre-S region of pDC101 to give the hybrid plasmid pDC103. Similarly, in accordance with the present invention, desired epitopes derived from the HDV genome, particularly those encoded in ORF5, may be provided with suitable EcoRI linkers and inserted in proper reading frame into the EcoRI site of pDC101, or used to replace the gD codons in the pDC103 hybrid, pDC103 is deposited with ATCC and has Accession No. 20726.

Hybrid particle immunogens are thus prepared using fused coding sequences for HBsAg and HDV and provide enhanced immunogenicity for the HDV epitopes.

D.6. Production of Antibodies to ORF5 Encoded Polypeptides

Antibodies to ORF5 encoded polypeptides are produced by immunizing an animal with partially purified ORF5 encoded polypeptides expressed in yeast strain AB110 (pYAG-δp1). The expression conditions and partial purification procedures for the yeast ORF5 products are those described supra. The polyclonal antibodies thereby derived may be purified from those directed against ORF5 encoded polypeptides by affinity chromatography, i.e., by passing the antiserum through affinity columns containing the expression products of the parental plasmid, pAB24. The antibodies to ORF5 products should be in the effluent. The techniques for preparing affinity columns are known to those of average skill in the art.

Utility

The invention disclosed herein has the following industrial uses. The information on the nucleotide sequence of the HDV genome may be used to design nucleotide probes which are useful for the diagnosis of HDV infection: these probes may also be used in diagnostic kits. The nucleotide sequence information may also be used to synthesize peptides and polypeptides which, in turn have the following uses. The peptides and polypeptides synthesized from ORF5 sequences, in particular, are useful for diagnosing HDV infections as reflected by the presence of HDV antibodies. Since ORF5 encodes the polypeptides comprising the HDV δ antigen. In addition, the products of expression of ORF5 sequences are useful in the production of vaccines to HDV, and in the preparation of HDV antibodies, both polyclonal and monoclonal. HDV antibodies directed against the ORF5 products may be used for the diagnosis of HDV antigens, based upon the presence of the antigens themselves, these antibodies may form the basis of diagnostic kits for HDV. In addition, the antibodies may also be used in vaccines against HDV.

The peptides or polypeptides synthesized from other ORF sequences may also be used to raise antibodies against HDV encoded components. These antibodies, as well as the ORF sequence products, may be useful in determining the viral replicative cycle and the cellular interactions with the viral components. This knowledge, in turn, will be useful for the commercial development of vaccines against HDV.

We claim:

1. A vaccine composition comprising a pharmaceutically acceptable excipient and an isolated hepatitis D virus $p24^\delta$ polypeptide.

2. The vaccine composition of claim 1 further comprising an adjuvant.

3. A vaccine composition comprising a pharmaceutically acceptable excipient and an isolated hepatitis D virus $p27^\delta$ polypeptide.

4. The vaccine composition of claim 3 further comprising an adjuvant.

\* \* \* \* \*